(12) United States Patent
Riehl et al.

(10) Patent No.: US 8,118,722 B2
(45) Date of Patent: Feb. 21, 2012

(54) REDUCING DISCOMFORT CAUSED BY ELECTRICAL STIMULATION

(75) Inventors: Mark Edward Riehl, Doylestown, PA (US); Kenneth Marc Ghiron, Allentown, PA (US)

(73) Assignee: Neuronetics, Inc., Malvern, PA (US)

(*) Notice: Subject to any disclaimer, the term of this patent is extended or adjusted under 35 U.S.C. 154(b) by 971 days.

(21) Appl. No.: 11/257,676

(22) Filed: Oct. 25, 2005

(65) Prior Publication Data

US 2006/0122454 A1 Jun. 8, 2006

Related U.S. Application Data

(63) Continuation-in-part of application No. 10/657,296, filed on Sep. 8, 2003, now Pat. No. 7,153,256.

(60) Provisional application No. 60/452,477, filed on Mar. 7, 2003.

(51) Int. Cl.
*A61N 1/00* (2006.01)
(52) U.S. Cl. .............................. 600/9; 600/13
(58) Field of Classification Search .................. 600/9–15
See application file for complete search history.

(56) References Cited

U.S. PATENT DOCUMENTS

| | | | |
|---|---|---|---|
| 3,683,923 A | 8/1972 | Anderson | 128/303.14 |
| 4,601,753 A | 7/1986 | Soileau et al. | |
| 4,712,558 A | 12/1987 | Kidd et al. | 128/421 |
| 4,940,453 A | 7/1990 | Cadwell | |
| 4,994,015 A | 2/1991 | Cadwell | 600/13 |
| 4,995,395 A | 2/1991 | Ilmoniemi et al. | 128/653 |
| 5,000,178 A * | 3/1991 | Griffith | 607/2 |
| 5,047,005 A | 9/1991 | Cadwell | |
| 5,061,234 A | 10/1991 | Chaney | |
| 5,078,674 A | 1/1992 | Cadwell | 600/13 |
| 5,097,833 A | 3/1992 | Campos | 128/421 |
| 5,116,304 A | 5/1992 | Cadwell | 600/13 |
| 5,120,961 A | 6/1992 | Levin et al. | |
| 5,154,723 A | 10/1992 | Kubota et al. | |

(Continued)

FOREIGN PATENT DOCUMENTS

EP 0998958 B1 12/2000

(Continued)

OTHER PUBLICATIONS

Baudewig, J. et al., "Functional MRI of Cortical Activations Induced by Transcranial Magnetic Stimulation(TMS)", *Brain Imaging-NeuroReport*, 2001, 12(16), 3543-3548.

(Continued)

*Primary Examiner* — John Lacyk
*Assistant Examiner* — Carrie R Dorna
(74) *Attorney, Agent, or Firm* — Condo Roccia LLP

(57) ABSTRACT

The invention is directed to a novel method for reducing discomfort caused by transcutaneous stimulation. The novel method includes providing transcutaneous stimulation, reducing the transcutaneous stimulation at a first location, and substantially maintaining the transcutaneous stimulation at a second location. The transcutaneous stimulation may be created by electric and/or magnetic fields. The first location may be relatively proximate to the cutaneous surface and may comprise tissue, nerves and muscle. Also, the second location may be relatively deeper than the first location and include, for example, brain tissue that requires the transcutaneous stimulation for treatment purposes. The invention further may include locating a conductor on a treatment area and/or a transcutaneous stimulation device relative to the first location. In addition, the method may further include adjusting how much the transcutaneous stimulation is reduced at the first location.

35 Claims, 29 Drawing Sheets

U.S. PATENT DOCUMENTS

| | | | | |
|---|---|---|---|---|
| 5,269,746 A * | 12/1993 | Jacobson | | 600/13 |
| 5,299,569 A | 4/1994 | Wernicke et al. | | 607/45 |
| 5,541,382 A | 7/1996 | Taylor et al. | | |
| 5,655,534 A | 8/1997 | Ilmoniemi | | |
| 5,707,334 A | 1/1998 | Young | | 600/9 |
| 5,725,471 A | 3/1998 | Davey et al. | | |
| 5,766,124 A | 6/1998 | Polson | | |
| 5,769,778 A | 6/1998 | Abrams et al. | | 600/14 |
| 5,813,970 A | 9/1998 | Abrams et al. | | 600/14 |
| 5,815,277 A | 9/1998 | Zare et al. | | |
| 5,830,132 A | 11/1998 | Robinson | | |
| 5,871,517 A | 2/1999 | Abrams et al. | | |
| 5,945,011 A | 8/1999 | Takano et al. | | |
| 5,984,854 A | 11/1999 | Ishikawa et al. | | |
| 5,984,856 A * | 11/1999 | Love | | 600/15 |
| 6,057,373 A | 5/2000 | Fogel | | 514/740 |
| 6,066,084 A | 5/2000 | Edrich et al. | | 600/13 |
| 6,117,066 A | 9/2000 | Abrams et al. | | 600/14 |
| 6,155,966 A | 12/2000 | Parker | | 600/13 |
| 6,169,963 B1 | 1/2001 | Markov | | 702/57 |
| 6,179,769 B1 | 1/2001 | Ishikawa et al. | | 600/9 |
| 6,179,770 B1 | 1/2001 | Mould | | |
| 6,179,771 B1 | 1/2001 | Mueller | | 600/13 |
| 6,198,958 B1 | 3/2001 | Ives et al. | | 600/411 |
| 6,253,109 B1 | 6/2001 | Gielen | | 607/45 |
| 6,256,531 B1 | 7/2001 | Ilmoniemi et al. | | 600/544 |
| 6,266,556 B1 | 7/2001 | Ives et al. | | |
| 6,278,889 B1 | 8/2001 | Robinson | | |
| 6,355,049 B1 | 3/2002 | Gill | | |
| 6,366,814 B1 | 4/2002 | Boveja et al. | | 607/45 |
| 6,389,318 B1 | 5/2002 | Zarinetchi et al. | | 607/61 |
| 6,402,678 B1 | 6/2002 | Fischell et al. | | 600/13 |
| 6,413,263 B1 | 7/2002 | Lobdill et al. | | |
| 6,425,852 B1 | 7/2002 | Epstein et al. | | |
| 6,434,410 B1 | 8/2002 | Cordero et al. | | |
| 6,463,328 B1 | 10/2002 | John | | 607/45 |
| 6,480,743 B1 | 11/2002 | Kirkpatrick et al. | | 607/45 |
| 6,484,059 B2 | 11/2002 | Gielen | | 607/45 |
| 6,488,617 B1 | 12/2002 | Katz | | 600/26 |
| 6,497,648 B1 | 12/2002 | Rey | | 600/14 |
| 6,500,110 B1 | 12/2002 | Davey et al. | | |
| 6,503,187 B1 | 1/2003 | Ilmoniemi et al. | | 600/14 |
| 6,516,288 B2 | 2/2003 | Bagne | | 702/179 |
| 6,537,197 B1 | 3/2003 | Ruohonen et al. | | 600/13 |
| 6,551,233 B2 | 4/2003 | Perreault et al. | | |
| 6,560,490 B2 | 5/2003 | Grill et al. | | 607/72 |
| 6,567,702 B1 | 5/2003 | Nekhendzy et al. | | 607/46 |
| 6,571,123 B2 | 5/2003 | Ives et al. | | 600/544 |
| 6,572,528 B2 | 6/2003 | Rohan et al. | | 600/14 |
| 6,591,138 B1 | 7/2003 | Fischell et al. | | |
| 6,629,935 B1 | 10/2003 | Miller et al. | | 600/558 |
| 6,663,556 B2 | 12/2003 | Barker | | 600/14 |
| 6,671,555 B2 | 12/2003 | Gielen et al. | | |
| 6,827,681 B2 | 12/2004 | Tanner et al. | | 600/9 |
| 6,849,040 B2 | 2/2005 | Ruohonen et al. | | 600/14 |
| 6,978,179 B1 | 12/2005 | Flagg et al. | | 607/45 |
| 2001/0031906 A1 | 10/2001 | Ishikawa et al. | | 600/13 |
| 2002/0013612 A1 | 1/2002 | Whitehurst | | 607/45 |
| 2002/0016534 A1 | 2/2002 | Trepagnier et al. | | |
| 2002/0087201 A1 | 7/2002 | Firlik et al. | | 607/45 |
| 2002/0091419 A1 | 7/2002 | Firlik et al. | | 607/45 |
| 2002/0103515 A1 | 8/2002 | Davey et al. | | 607/66 |
| 2002/0123780 A1 | 9/2002 | Grill et al. | | 607/72 |
| 2002/0160436 A1 | 10/2002 | Markov et al. | | 435/15 |
| 2002/0169355 A1 | 11/2002 | Rohan et al. | | 600/9 |
| 2003/0004392 A1 | 1/2003 | Tanner et al. | | 600/9 |
| 2003/0023159 A1 | 1/2003 | Tanner | | 600/417 |
| 2003/0028072 A1 | 2/2003 | Fischell et al. | | 600/13 |
| 2003/0050527 A1 | 3/2003 | Fox et al. | | 600/13 |
| 2003/0073899 A1 | 4/2003 | Ruohonen et al. | | 600/417 |
| 2003/0074032 A1 | 4/2003 | Gliner et al. | | 607/45 |
| 2003/0080827 A1 | 5/2003 | Chominski | | |
| 2003/0082507 A1 | 5/2003 | Stypulkowski | | 434/262 |
| 2003/0087264 A1 | 5/2003 | Kaplitt et al. | | 435/6 |
| 2003/0088274 A1 | 5/2003 | Gliner et al. | | 607/3 |
| 2003/0097161 A1 | 5/2003 | Firlik et al. | | 607/72 |
| 2003/0125786 A1 | 7/2003 | Gliner et al. | | 607/116 |
| 2003/0130706 A1 | 7/2003 | Sheffield et al. | | 607/46 |
| 2003/0195588 A1 | 10/2003 | Fischell et al. | | 670/55 |
| 2003/0204135 A1 | 10/2003 | Bystritsky | | 600/407 |
| 2004/0010177 A1 | 1/2004 | Rohan et al. | | 600/9 |
| 2004/0019370 A1 | 1/2004 | Gliner et al. | | |
| 2004/0077921 A1 | 4/2004 | Becker et al. | | 600/9 |
| 2004/0122281 A1 * | 6/2004 | Fischell et al. | | 600/13 |
| 2004/0127942 A1 | 7/2004 | Yomtov et al. | | 607/3 |
| 2004/0138524 A1 | 7/2004 | Ueda et al. | | |
| 2004/0138550 A1 | 7/2004 | Hartlep et al. | | 600/407 |
| 2004/0138578 A1 | 7/2004 | Pineda et al. | | |
| 2004/0143300 A1 | 7/2004 | Rogers | | 607/45 |
| 2004/0153129 A1 | 8/2004 | Pless et al. | | 607/62 |
| 2004/0204625 A1 | 10/2004 | Riehl et al. | | |
| 2005/0021104 A1 | 1/2005 | DiLorenzo | | 607/45 |
| 2005/0124848 A1 | 6/2005 | Holzner | | 600/9 |
| 2005/0216071 A1 | 9/2005 | Devlin et al. | | 607/48 |
| 2005/0228209 A1 | 10/2005 | Schneider et al. | | 600/13 |
| 2005/0256539 A1 | 11/2005 | George et al. | | 607/2 |

FOREIGN PATENT DOCUMENTS

| | | |
|---|---|---|
| EP | 1 273 320 A1 | 1/2003 |
| EP | 1335199 A1 | 8/2003 |
| JP | 62-009880 | 1/1987 |
| JP | S62-197073 | 8/1987 |
| JP | 01-146545 | 6/1989 |
| JP | 04-048205 | 2/1992 |
| JP | 07-067972 | 3/1995 |
| JP | 08-057063 | 3/1996 |
| WO | 99/55421 | 11/1999 |
| WO | WO 99/64884 | 12/1999 |
| WO | WO 00/74777 | 12/2000 |
| WO | WO 01/12236 A2 | 2/2001 |
| WO | WO 01/28622 A2 | 4/2001 |
| WO | WO 01/97906 A2 | 12/2001 |
| WO | WO 02/09811 A1 | 2/2002 |
| WO | WO 02/31604 A1 | 4/2002 |
| WO | WO 02/32504 A2 | 4/2002 |
| WO | WO 02/072194 A2 | 9/2002 |
| WO | WO 02/084237 A1 | 10/2002 |
| WO | WO 02/085449 A2 | 10/2002 |
| WO | WO 02/085454 A1 | 10/2002 |
| WO | 02/089902 | 11/2002 |
| WO | WO 02/089902 A2 | 11/2002 |
| WO | WO 02/094997 A2 | 11/2002 |
| WO | WO 03/035163 A2 | 5/2003 |
| WO | WO 03/039468 A2 | 5/2003 |
| WO | WO 03/082405 A1 | 10/2003 |
| WO | WO 03/084605 A1 | 10/2003 |
| WO | WO 03/085546 A1 | 10/2003 |
| WO | WO 03/090604 A2 | 11/2003 |
| WO | WO 03/098268 A1 | 11/2003 |
| WO | WO 2004/006750 A2 | 1/2004 |
| WO | WO 2004/080527 A2 | 9/2004 |
| WO | WO 2004/082759 A2 | 9/2004 |
| WO | WO 2004/100765 A2 | 11/2004 |
| WO | WO 2005/000401 A1 | 1/2005 |
| WO | WO 2005/004712 A1 | 1/2005 |
| WO | WO 2005/065768 A1 | 7/2005 |
| WO | WO 2007/123147 A1 | 11/2007 |

OTHER PUBLICATIONS

Bohning, D.E. et al., "A TMS Coil Positioning/Holding System for MR Image-Guided TMS Interleaved with fMRI", *Clinical Neurophysiology*, 2003, 114, 2210-2219.

Bohning, D.E. Ph.D. et al., "A Combined TMS/fMRI Study of Intensity-Dependant TMS over Motor Cortex", *Society of Biological Psychiatry*, 1999, 45, 385-394.

Bohning, D.E. Ph.D. et al., "BOLD-fMRI Response to Single-Pulse Transcranial Magnetic Stimulation (TMS)", *Journal of Magnetic Resonance Imaging*, 2000, 11, 569-574.

Garcia-Toro, M. et al., "Modest Adjunctive Benefit with Transcranial Magnetic Stimulation in Medication-Resistant Depression", *Journal of Affective Disorders*, 2001, 64, 271-275.

George, M.S. et al., "A Controlled Trial of Daily Left Prefrontal Cortex TMS for Treating Depression", *Society of Biological Psychiatry*, 2000, 48, 962-970.

George, M.S. "New Methods of Minimally Invasive Brain Modulation as Therapies in Psychiatry: TMS,MST,VNS and DBS", *Chinese Medical Journal* (Taipei), 2002, 65, 349-360.

Grafman, J. Ph.D., "TMS as a Primary Brain Mapping Tool" *Transcranial Magnetic Stimulation in Neuropsychiatry*, 2000, 115-140.

Nahas, Z. et al., "Left Prefrontal Transcranial Magnetic Stimulation(TMS) Treatment of Depression in Bipolar Affective Disorder: A Pilot Study of Acute Safety and Efficacy", *Bipolar Disorders*, 2003, 5, 40-47.

Lisanby, S.H. MD. et al., "Magnetic Seizure Therapy of Major Depression", *Arch Gen Psychiatry*, 2001, 58, 303-307.

Lisanby, S.H. et al., "Sham TMS: Intracerebral Measurement of the Induced Electrical Field and the Induction of Motor-Evoked Potentials", *Society of Biological Psychiatry*, 2001, 49, 460-463.

Lisanby, S.H., "Safety and Feasibility of Magnetic Seizure Therapy(MST) in Major Depression: Randomized Within-Subject Comparasion with Electroconvulsive Therapy", *Neuropsychopharmacology, New York State Psychiatric Institute*, 2003, 28, 1852-1865.

Lisanby, S.H., "Update on Magnetic Seizure Therapy: A Novel Form of Convulsive Therapy", *The Journal of ECT*, 2002, 18, 182-188.

Lorberbaum, J.P., M.D. et al., "Safety Concerns of TMS", *Transcranial Magnetic Stimulation in Neuropsychiatry*, 2000, 141-161.

Loo, C.K. et al., "Transcranial Magnetic Stimulation (TMS) in Controlled Treatment Studies: Are Some "Sham" Forms Active?", *Society of Biological Psychiatry*, 2000, 47, 325-331.

Nahas, Z. et al., "Unilateral Left Prefrontal Transcranial Magnetic Stimulation(TMS) Produces Intensity-Dependent Bilateral Effects as Measured by Interleaved BOLD fMRI", *Society of Biological Psychiatry*, 2001, 50, 712-720.

Pridmore, S., "Substitution of Rapid Transcranial Magnetic Stimulation Treatments for Electroconvulsive Therapy Treatments in a Course of Electroconvulsive Therapy", *depression and Anxiety*, 2000, 12, 118-123.

Roth, Y. et al., "A Coil Design for Transcranial Magnetic Stimulation of Deep Brain Regions", *Journal of Clinical Neurophysiology*, 2002, 19(4), 361-370.

Ruohonen, J., "Electroencephalography Combined with TMS", BioMag Laboratory, Helsinki University Central Hospital, http://www.biomag.helsinki.fi/tms/TMSEEG.html, Oct. 6, 1999, 22 pages.

Terrace, H.S. et al., "The Cognitive Effects of Electroconvulsive Shock and Magnetic Seizure Therapy in Rhesus Monkeys", *Society for Neuroscience Abstract Viewer and Itinerary Planner*, 2002, Abstract Only # 184.14.

Terrace, H.S. et al., "The Cognitive Effects of Electroconvulsive Shock Stimulation and Magnetic Seizure Therapy in Rhesus Monkeys", *Society for Neuroscience Abstracts*, 2001, 27(1), 536.7, p. 1418.

Trivedi, M.H., MD., "Treatment-Resistant Depression: New Therapies on the Horizon", *Annals of Clinical Psychiatry*, 2003, 15(1), 59-70.

Hess, C.W. et al., "Magnetic Stimulation of the Human Brain: Influence of Size and Shape of the Stimulating Coil", *Motor Disturbances II*, 1990, 3, 31-42.

Wassermann, E.M., "Repetitive Transcranial Magnetic Stimulation: An Introduction and Overview", *CNS Spectrums, The International Journal of Neuropsychiatric Medicine*, Jan. 1997, 7 pages.

Japanese Patent Application No. 2006-509153: English Translation of Notice of Reason of Refusal dated Nov. 4, 2009, 3 pages.

Japanese Patent Application No. 2006-509170: English Translation of Notice of Reason of Refusal dated Jul. 20, 2010, 2 pages.

U.S. Appl. No. 10/657,296: Notice of Allowance and Fee(s) Due, dated Sep. 29, 2006, 6 pages.

U.S. Appl. No. 10/657,296: Non-Final Rejection, dated Jul. 26, 2006, 5 pages.

U.S. Appl. No. 10/657,296: Non-Final Rejection, dated Jun. 16, 2005, 7 pages.

U.S. Appl. No. 10/729,243: Notice of Allowance and Fee(s) Due, dated Aug. 27, 2009, 6 pages.

U.S. Appl. No. 10/729,243: Final Rejection, dated Apr. 7, 2008, 5 pages.

U.S. Appl. No. 10/729,243: Non-Final Rejection, dated Jun. 16, 2005, 16 pages.

U.S. Appl. No. 10/792,994:, Notice of Allowance and Fee(s) Due, dated Jun. 25, 2007, 6 pages.

U.S. Appl. No. 10/792,994: Final Rejection, dated Dec. 13, 2006, 8 pages.

U.S. Appl. No. 10/792,994: Non-Final Rejection, Dated Mar. 24, 2006, 7 pages.

U.S. Appl. No. 10/792,994: Notice of Allowance and Fee(s) Due, dated Dec. 20, 2005, 4 pages.

U.S. Appl. No. 10/792,994: Non-Final Rejection, dated Jun. 16, 2005, 14 pages.

U.S. Appl. No. 10/672,833: Non-Final Rejection, dated May 15, 2007, 25 pages.

U.S. Appl. No. 10/672,833: Final Rejection, dated Nov. 14, 2008, 15 pages.

Youcef-Toumi et al., "Noninvasive Blood Glucose Analysis using Near Infrared Absorption Spectroscopy", The Home Automation and Healthcare Consortium, Progress Report No. 2-3, Mar. 31, 1999, pp. 1-8.

* cited by examiner

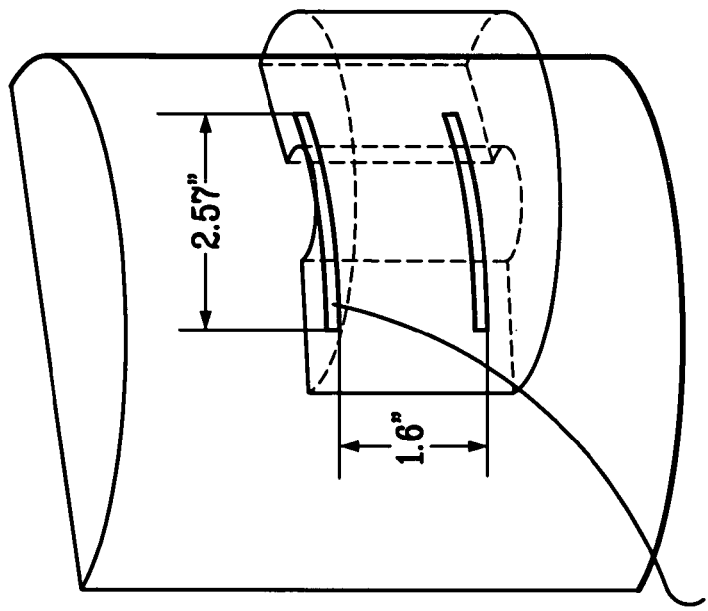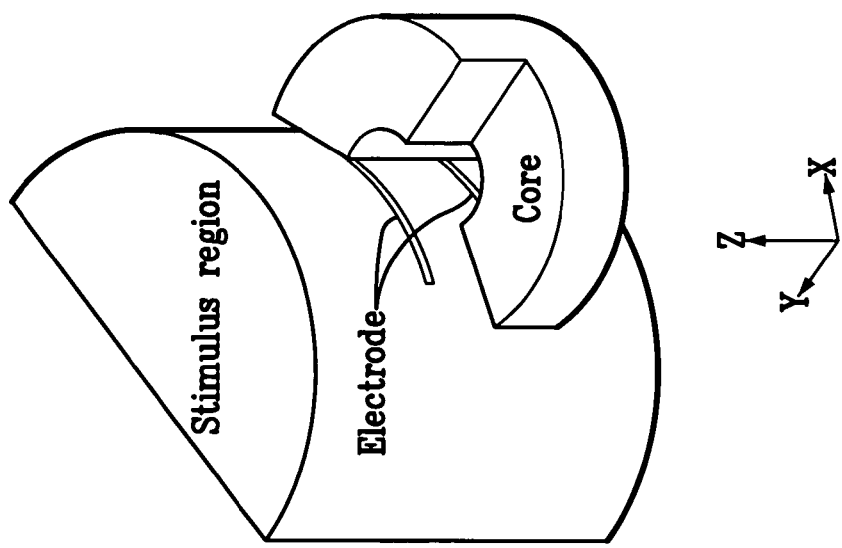
FIG. 21

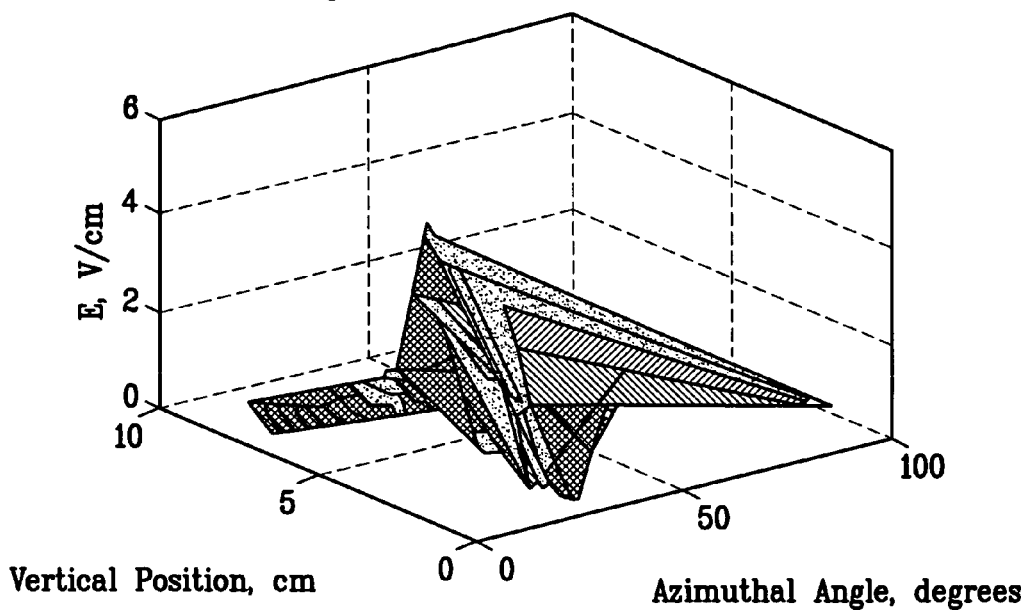
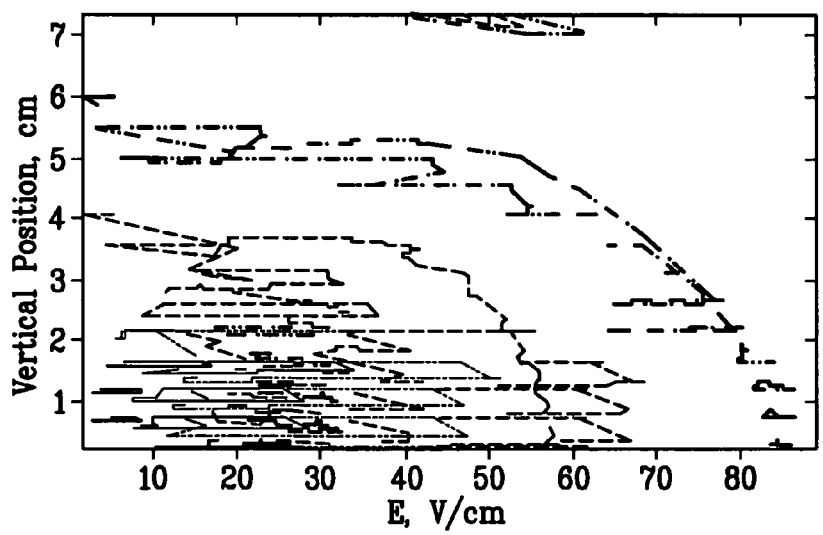
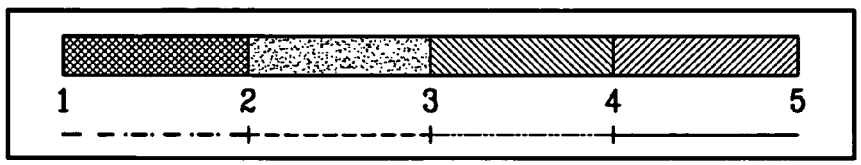
FIG. 22B

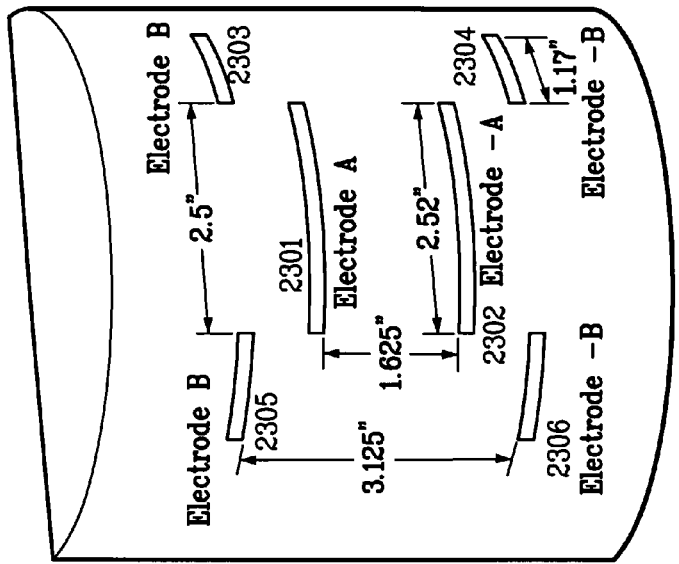
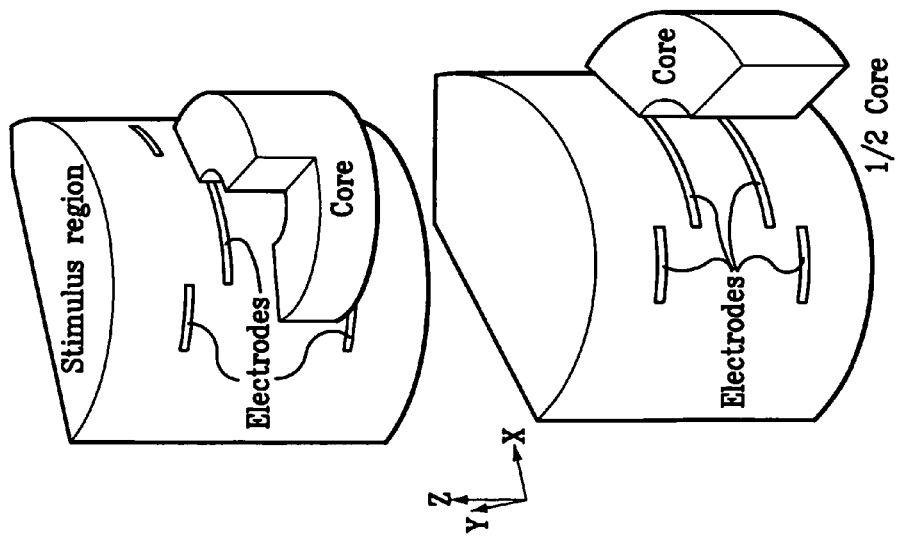
FIG. 23

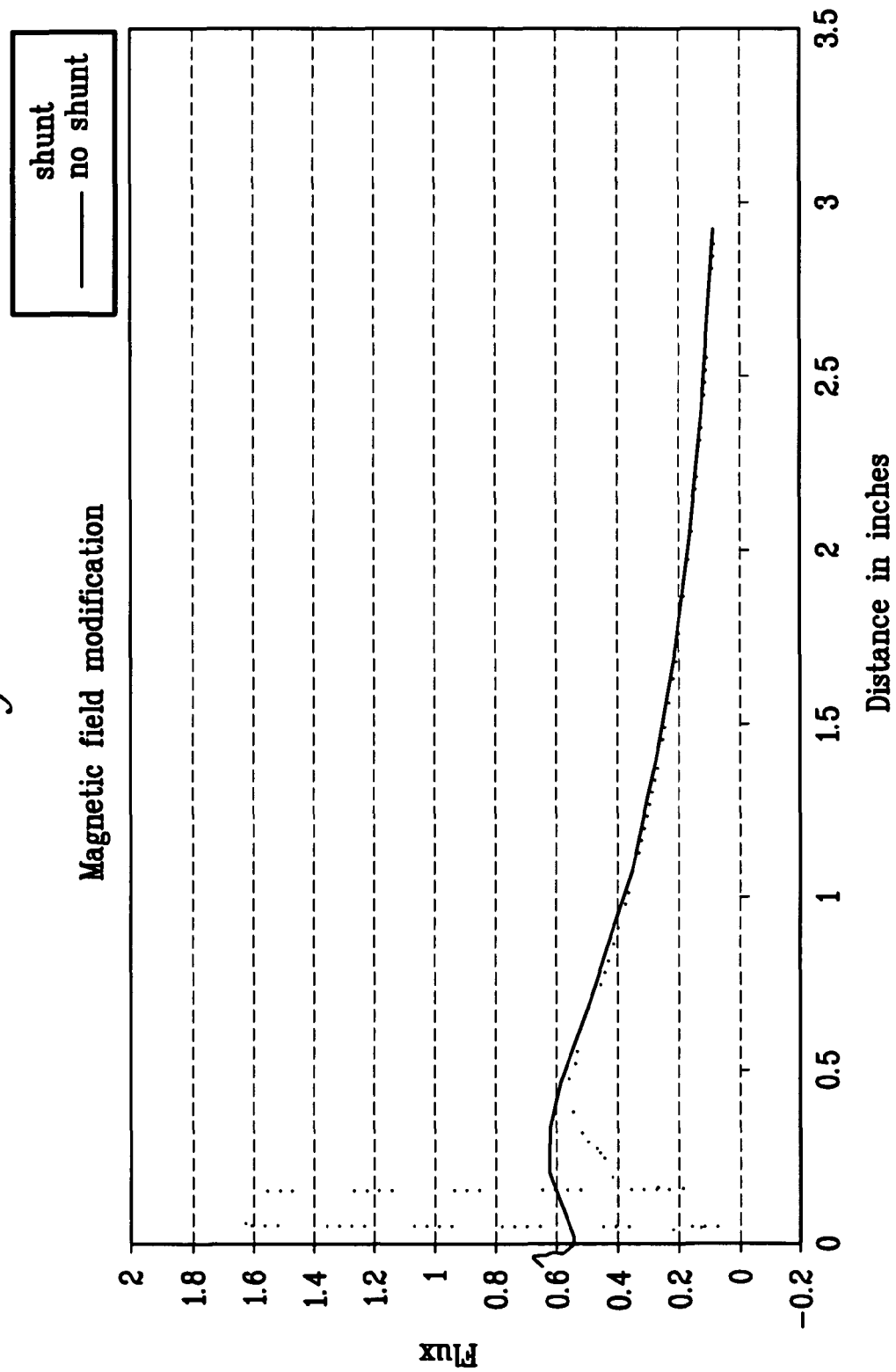

REDUCING DISCOMFORT CAUSED BY ELECTRICAL STIMULATION

CROSS-REFERENCE TO RELATED APPLICATION

This application claims priority under 35 U.S.C. §119 (e) from U.S. provisional application Ser. No. 60/452,477, filed on Mar. 7, 2003, entitled "Device, Method, and System for the Reduction of Discomfort Associated with and Facilitating Treatment via Magnetic Stimulation," which is herein incorporated by reference in its entirety. This application is a continuation-in-part of U.S. patent application Ser. No. 10/657,296, filed Sep. 8, 2003 entitled "Reducing Discomfort Caused by Electrical Stimulation," which is herein incorporated by reference in its entirety.

FIELD OF THE INVENTION

The invention relates to the field of electrical stimulation. Specifically, the invention relates to reducing discomfort created by electrical stimulation.

BACKGROUND OF THE INVENTION

A number of medical ailments are treated or treatable through the application of electrical stimulation to an afflicted portion of a patient's body. Two examples of electrical stimulation may include magnetic or inductive stimulation which may make use of a changing magnetic field, and electric or capacitive stimulation in which an electric field may be applied to the tissue. Neurons, muscle and tissue cells are all forms of biological circuitry capable of carrying electrical signals and responding to electrical stimuli. For example, when an electrical conductor is passed through a magnetic field, an electric field is induced causing current to flow in the conductor. Because various parts of the body also act as a conductor, when a changing magnetic field is applied to the portion of the body, an electric field is created causing current to flow. In the context of biological tissue, for example, the resultant flow of electric current stimulates the tissue by causing neurons in the tissue to depolarize. Also, in the context of muscles, for example, muscles associated with the stimulated neurons contract. In essence, the flow of electrical current allows the body to simulate typical and often desired chemical reactions.

Electrical stimulation has many beneficial and therapeutic biological effects. For example, the use of magnetic stimulation is effective in rehabilitating injured or paralyzed muscle groups. Another area in which magnetic stimulation is proving effective is treatment of the spine. The spinal cord is difficult to access directly because vertebrae surround it. Magnetic stimulation may be used to block the transmission of pain via nerves in the back (e.g., those responsible for lower back pain). Further, unlike the other medical processes that stimulate the body, electrical stimulation may be non-invasive. For example, using magnetic fields to generate current in the body produces stimulation by passing the magnetic field through the skin of a patient.

Magnetic stimulation also has proven effective in stimulating regions of the brain, which is composed predominantly of neurological tissue. One area of particular therapeutic interest is the treatment of neuropsychiatric disorders. It is believed that more than 28 million people in the United States alone suffer from some type of neuropsychiatric disorder. These include specific conditions such as depression, schizophrenia, mania, obsessive-compulsive disorder, panic disorders, just to name a few. One particular condition, depression, is the often referred to as the "common cold" of psychiatric disorders, believed to affect 19 million people in the United States alone, and possibly 340 million people worldwide. Modern medicine offers depression patients a number of treatment options, including several classes of anti-depressant medications like selective serotonin reuptake inhibitors (SSRI), MAIs, tricyclics, lithium, and electroconvulsive therapy (ECT). Yet many patients remain without satisfactory relief from the symptoms of depression. To date, ECT remains the "gold standard" of treatments for severe depression; however, many patients will not undergo the procedure because of its severe side effects.

Recently, repetitive transcranial magnetic stimulation (rTMS) has been shown to have significant anti-depressant effects for patients, even those that do not respond to the traditional methods and medications. In one embodiment of rTMS, a subconvulsive stimulation is applied to the prefrontal cortex in a repetitive manner, causing a depolarization of cortical neuron membranes. The membranes are depolarized by the induction of small electric fields, usually in excess of 1 volt per centimeter (V/cm). These small electric fields result from a rapidly changing magnetic field applied non-invasively.

It is now well known to those skilled in the art that both the left and right prefrontal cortex regions of the brain have strong communication links to Limbic System structures, which contain the "circuits" controlling mood and general behavior. One objective of rTMS is to provide stimulation to these biological circuits through a non-invasive, sub-convulsive technique to relieve the symptoms of depression without many of the negative side effects of ECT or medications. However, one reported side effect of rTMS for the treatment of depression is patient discomfort at the site of the stimulation. This discomfort is caused, in part, by the depolarization of neuron membranes in the scalp and the resulting scalp muscle contractions that occur at the frequency of the rTMS. Testing has shown that approximately 25% of rTMS patients report this discomfort to be at a level that is very uncomfortable. In general, the greater the power and the higher the frequency of the therapeutic magnetic stimulation, the more discomfort is reported. Yet, reducing the power levels may not be a viable option because greater power has been shown to desirably stimulate deeper structures. Also, relatively higher frequencies (e.g., greater than 1 Hertz (Hz)) have been shown to have a greater anti-depressant effect.

Therefore, it is desirable to develop techniques for reducing discomfort caused by electrical stimulation.

SUMMARY OF THE INVENTION

The invention is directed to a novel method for reducing discomfort caused by transcutaneous stimulation. The novel method includes providing transcutaneous stimulation, reducing the transcutaneous stimulation at a first location, and substantially maintaining the transcutaneous stimulation at a second location. The transcutaneous stimulation may be created by electric and/or magnetic fields. The first location may be relatively proximate to the cutaneous surface and may comprise tissue, nerves and muscle. Also, the second location may be relatively deeper than the first location and include, for example, brain tissue that requires the transcutaneous stimulation for treatment purposes. The invention further may include locating a conductor on a treatment area and/or a transcutaneous stimulation device relative to the first location. In addition, the method may further include adjusting how much the transcutaneous stimulation is reduced at the first location. Such adjusting of the transcutaneous stimulation may be accomplished by applying a signal at the first location. The signal may be inversely proportional to another signal used to create the transcutaneous stimulation.

BRIEF DESCRIPTION OF THE DRAWINGS

FIGS. 20 and 21 illustrate an example configuration for the placement of two conductors for reducing discomfort caused by transcutaneous stimulation;

FIGS. 23 and 24 illustrate an embodiment with six conductors used to reduce the fields created by a magnetic core device for reducing discomfort caused by transcutaneous stimulation;

FIG. 27 is a graphical depiction of the effect of conductors on the magnetic field as a function of distance.

DETAILED DESCRIPTION OF ILLUSTRATIVE EMBODIMENTS

Overview

In 1831, Michael Faraday discovered that the magnitude of an electric field induced on a conductor is proportional to the rate of change of magnetic flux density that cuts across the conductor. Faraday's law, well known to those skilled in the art may be represented as $E \sim -(dB/dt)$, where E is the induced electric field in volts/meter, dB/dt is the time rate of change of magnetic flux density in Tesla/second. In other words, the amount of electric field induced in an object like a conductor is determined by two factors: the magnetic flux density and the time rate of change of the flux density. The greater the flux density and its derivative, the greater the induced electric field and resulting current density. Because the magnetic flux density decreases in strength as the square of the distance from the source of the magnetic field, the flux density is greater the closer the conductor is to the source of the magnetic field. When the conductor is a coil, the current induced in the coil by the electric field may be increased in proportion to the number of turns of the coil.

When the electric field is induced in a conductor, the electric field creates a corresponding current flow in the conductor. The current flow is in the same direction of the electric field vector at a given point. The peak electric field occurs when dB/dt is the greatest and diminishes at other times. If the electric field decreases, for example after a magnetic pulse, the current flows in a direction that tends to preserve the electric field (i.e., Lenz's Law).

In the context of electrical stimulation of the anatomy, certain parts of the anatomy (e.g., nerves, tissue, muscle, brain) act as a conductor and carry electric current when an electric field is presented. The electric field may be presented to these parts of the anatomy transcutaneously by applying a time varying (e.g., pulsed) magnetic field to the portion of the body. For example, in the context of TMS, a time-varying magnetic field may be applied across the skull to create an electric field in the brain tissue, which produces a current. If the induced current is of sufficient density, neuron membrane potential may be reduced to the extent that the membrane sodium channels open and an action potential response is created. An impulse of current is then propagated along the axon membrane which transmits information to other neurons via modulation of neurotransmitters. Such magnetic stimulation has been shown to acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations and metabolism so that depression is alleviated.

Systems and Methods of Reducing Discomfort

Figure 1:
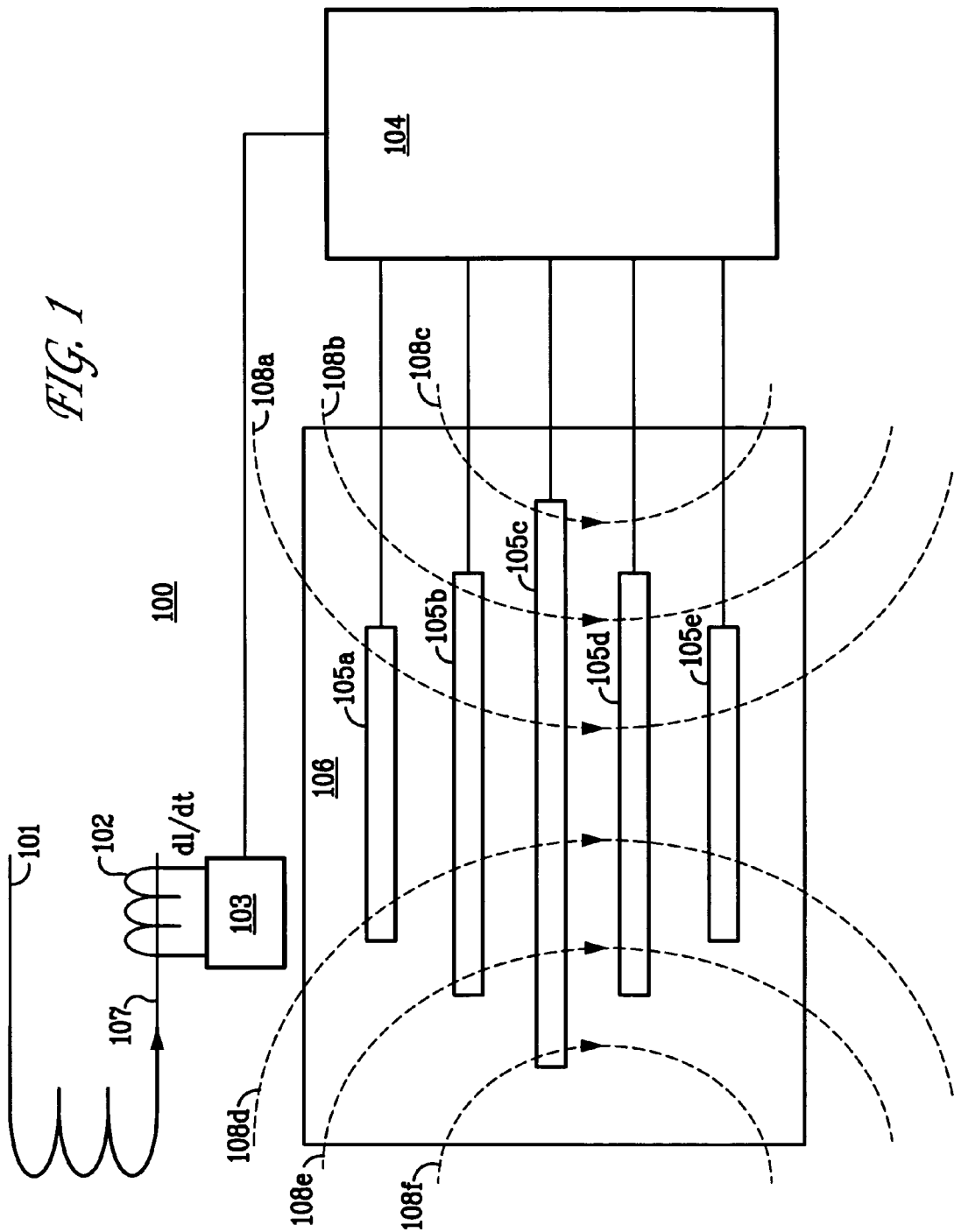
FIG. 1 is a block diagram illustrating a technique for reducing discomfort caused by transcutaneous stimulation.

FIG. 1 is a block diagram illustrating a technique for reducing discomfort caused by electrical stimulation. As shown in FIG. 1, a system 100 includes a magnet stimulation circuit 101. Magnet stimulation circuit 101 is an electric circuit that provides a power signal to a main magnet (not shown). The power signal may be any time-varying electric signal capable of generating an electric and/or magnetic field. The main magnet may be used to conduct transcranial magnetic stimulation (TMS) and/or repetitive transcranial magnetic stimulation (rTMS) as described in U.S. Pat. Nos. 5,725,471, 6,132,361 6,086,525 and 6,425,852, and incorporated herein by reference.

In the following description, for purposes of explanation and not limitation, specific details are set forth regarding system 100 and other systems, methods and techniques for reducing discomfort caused by electric stimulation. For example, particular components, component configurations and placements, devices, techniques, etc. are described in detail. However, it should be appreciated that the invention is not meant to be limited to these examples. The examples, components, etc. are provided simply to provide an understanding of the invention. It will be apparent to one skilled in the art that the invention may be practiced in other embodiments that depart from these specific details. Detailed descriptions of well-known devices, components, techniques, etc. are omitted so as not to obscure the description of the invention.

System 100 includes an inductive device 102. Inductive device 102 operates to receive a current induced upon it by a wire 107 that carries a current (I) in magnet stimulation circuit 101. The current induced on inductive device 102 by wire 107 is proportional to the time derivative of the current (I) in magnet stimulation circuit 101, based on principles of electrical induction well known to those skilled in the art. Inductive device 102 may be any device that is capable of having a current induced thereon, including for example a coil of wire and/or a current transformer, well known to those skilled in the art. Inductive device 102 may be in communication with an amplifier 103. Amplifier 103 is in communication with a signal processor 104. Signal processor 104 is in communication with a series of conductors 105a-e. Conductors 105 may be small electrodes, having small cross section so as to minimize heating from induced eddy currents. Typical maximum dimension may be approximately 5 mm. The shape of the electrodes is determined by the geometry of the electric field induced in the surface tissue. When in use, the electrodes are in electrical contact with the surface tissue, typically through a conductive gel which reduces the contact impedance to less than approximately 20 kOhms. Also, conductors 105 may be affixed to a flexible circuit pad 106.

Flexible circuit pad 106 may be made of a MYLAR™, polyester, or other polymer-type material that permits the pad and thus conductors 105 to fit the contours of the treatment area on the patient and/or to fit the contours of the magnetic stimulation device (e.g., magnet with ferromagnetic core). Flexible circuit pad 106 also may have an adhesive material that permits the pad, and therefore conductors 105, to be affixed to a location in which system 100 is to operate. Also, flexible circuit pad 106 may have a conductive gel that facilitates conduction of electrical energy between conductors 105 and the treatment area. The conductive gel may be covered with a removable paper or plastic seal (not shown), which when removed permits the conductive gel to come into contact with the treatment area.

Flexible circuit pad 106 may include a connector that permits components of system 100 (e.g., signal processor 104) to be readily attached and disconnected therefrom. In addition, flexible circuit pad 106 may have certain insulating materials to prevent undesirable conducting of electrical energy with the patient and/or with components of system 100.

Flexible circuit pad 106 also may include electrical or physical disposal mechanisms that require a new flexible circuit pad to be used with each treatment. Alternatively, the disposal mechanism may allow a certain flexible circuit pad a certain number of times and/or be used by a certain patient. Therefore, the disposal mechanism may prohibit undesirable re-usage of the flexible circuit pad 106, and therefore facilitate sanitary usage of flexible circuit pad 106 both for an individual patient and across numerous patients.

In operation, when main stimulation circuit 101 is provided power from an external power source (not shown) to conduct proper stimulation of the patient, current (I) travels through main stimulation circuit 101. Main stimulation circuit 101 is connected to a magnetic stimulation device (e.g., an electromagnet) (not shown) that creates a magnetic field or fields designed to provide treatment to a particular area on the patient. As shown in FIG. 1, providing power to the magnetic stimulation device creates magnetic fields 108a-f.

As discussed in U.S. Pat. Nos. 5,725,471, 6,132,361 6,086, 525 and 6,425,852, incorporated herein by reference, magnetic fields 108a-f act to stimulate nerves, tissue and muscle etc. in the patient for treatment or therapeutic purposes. Current (I) travels through magnetic stimulation circuit 101 and onto inductive device 102 via wire 107. It should be appreciated that inductive device 102 may be located in series with and/or in parallel with main stimulation circuit 101, or in any electrical direct or indirect communication configuration.

Inductive device 102 operates to sense a current (I) provided to magnet stimulation circuit 101 by receiving an induced electrical value that is based on the current (I) that passes to the magnetic stimulation circuit 101. For example, the value received by inductive device 102 may be an induced voltage that is proportional to a change in current (I) in amperes divided by the amount of time in which the change in current takes place. This is expressed mathematically as $E = L \, di/dt$, where E is the induced voltage, di is the change of current, dt is the amount of time in which the change in current takes place, and L represents the electrical inductive properties of the inductive device 102. In one embodiment, the induced voltage, for example, may then be provided to an amplifier 103. Amplifier 103 operates to manipulate (e.g., boost) the induced voltage E as required by system 100 and by signal processor 104.

Signal processor 104 receives the amplified induced voltage signal from amplifier 103 and may operate to further manipulate the signal depending on the characteristics of system 100. For example, signal processor 104 may operate to invert a polarity of the signal from amplifier 103. In this way, the magnetic and/or electric fields created by the magnetic stimulation device are in substantially opposite polarity to the magnetic and/or electric fields created by conductors 105.

Also, signal processor 104 may operate to ensure that the timing of the fields created by magnetic stimulation device and conductors 105 are generated substantially simultaneously. In particular, because signal processor 104 receives a signal from the circuitry that powers the magnetic stimulation device, signal processor 104 may operate to "gate" or activate the signal to conductors 105 at the same time the magnetic stimulation device is gated. In this way, the fields from the magnetic stimulation device are present at substantially the same time that the fields from conductors 105 are present. Synchronizing the fields may further facilitate the ability of the fields from conductors 105 eliminating or reducing the undesirable effects of the fields from the magnetic stimulation device.

Therefore, amplifier 103 and/or signal processor 104 further facilitate the cancellation of the fields from the magnetic stimulation device and conductors 105, as desired (e.g., at or near the scalp of a rTMS patient). The precise manipulation of the signal by signal processor 104 and/or amplifier 103 will depend upon many variables including the physical and electrical characteristics of system 100, of the patient and the treatment area, and of conductors 105, just to name a few. By receiving the signal from amplifier 103 and by understanding the characteristics of the other variables, signal processor 104 may be adapted to provide the proper signal timing and strength to conductors 105 so as to create the proper fields, at the proper time, in the proper location.

In just one embodiment in the context of rTMS or TMS, the stimulating magnet may be applied to a certain location on the patient's head so as to determine the minimum amount of induced current required to affect the particular patient's neurons. For example, the "test" location may be the patient's motor center as the results are easy to identify because a portion of the patient's body may move in response to the appropriate dosage. Once the proper dose is determined at the motor center, the stimulating magnet with attached flexible circuit pad 106 may be placed on the particular treatment location to affect the neurons required to treat the patient's depression.

Signal processor 104 may then provide the signal (e.g., a time-varying signal) to conductors 105. Providing the signal to conductors 105 causes a current to flow in conductors 105, which in turn creates an electric field that is generated proximate to each of the conductors. This electric field may be used to offset the electric and magnetic fields created by the magnetic stimulation device that create discomfort in the patient, without adversely impacting the desired therapeutic effect of those magnetic fields. For example, in the context of rTMS or TMS, the electric and/or magnetic fields created by conductors 105 may be designed to eliminate and/or reduce the magnetic fields created by the magnetic stimulation device at the surface of the scalp that create discomfort in the patient, without reducing the efficacy of the magnetic field created by the magnetic stimulation device within the area that is desired to be treated (e.g., the brain).

In order to ensure that the magnetic fields created by conductors 105 reduce the discomfort to the patient without diminishing the usefulness of the treatment, certain characteristics of system 100 may be varied. Although not meant to be exclusive such variances may include modifying the electrical characteristics (e.g., conductivity) and physical characteristics (e.g., surface area) of conductors 105. Signal processor 104 may be designed to scale the applied voltage signal up and/or down to a level that permits conductors 105 to reduce the discomfort caused by the magnetic stimulation device on the patient. Also, amplifier 103 may be designed to amplify the induced voltage signal up and/or down. It should be appreciated that system 100 may include any combination of varying the above-mentioned characteristics.

In addition to being dependent on the characteristics of system 100, how much and which system features vary may depend on the particular characteristics of the patient. For example, in the context of rTMS or TMS, such specific characteristics may include, but not be limited to, the shape and size of the patient's head, the amount and density of hair on the patient's head, the particular area of the cranium that is desired to be treated, etc.

Figure 2:
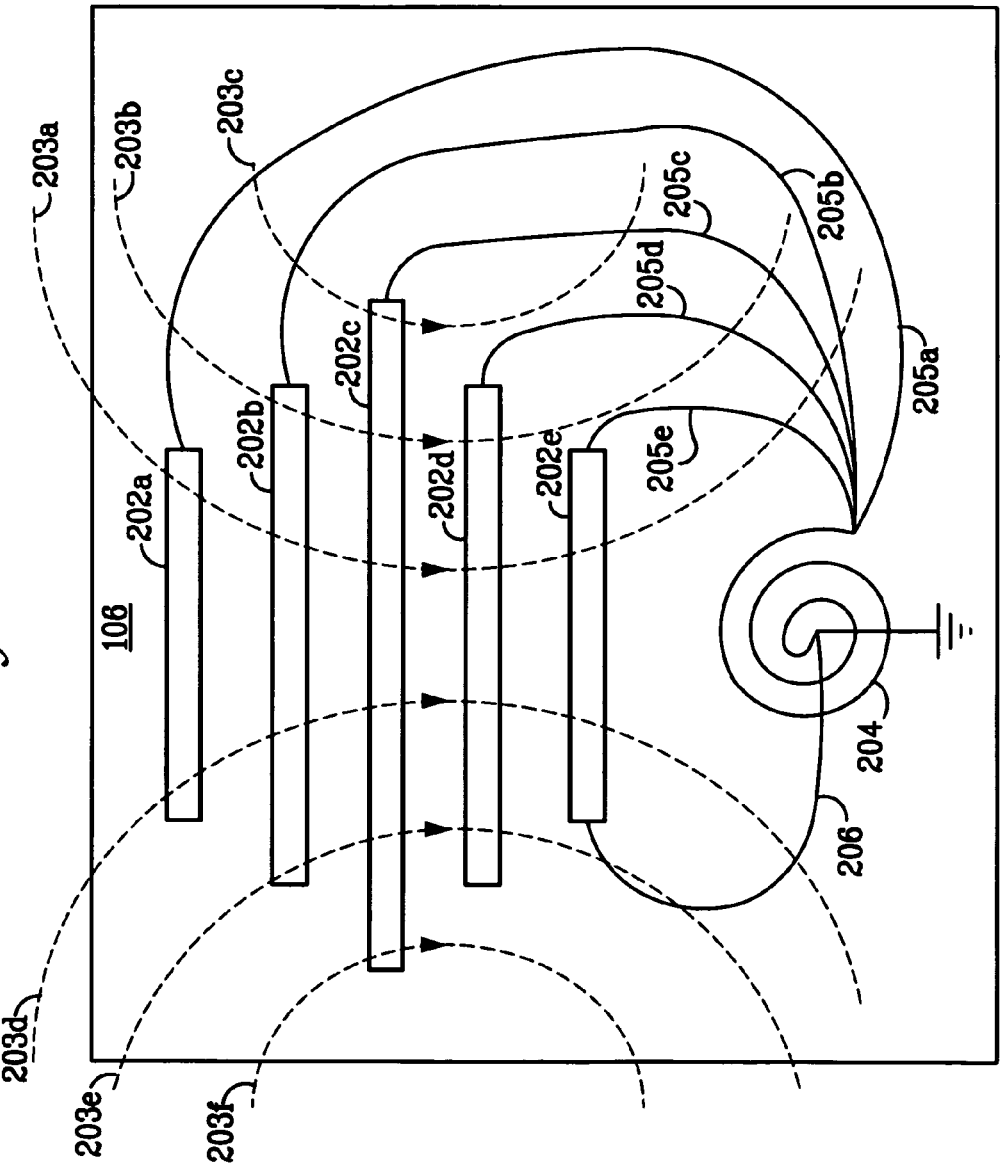
FIG. 2 is a block diagram illustrating another technique for reducing discomfort caused by transcutaneous stimulation.

FIG. 2 is a block diagram illustrating another technique for reducing discomfort caused by electrical stimulation. As shown in FIG. 2, a system 200 includes a flexible circuit pad 106 having a number of conductors 202a-e. Flexible circuit pad 106 may have an adhesive material that permits the pad, and therefore the conductors, to be affixed to a location in which system 200 is to operate. Conductors 202 may be small electrodes, having a maximum dimension of approximately 5 mm. Also, conductors may vary in their electrical characteristics (e.g, conductivity) and physical characteristics (e.g., size and shape) depending on their placement on flexible circuit pad 106 relative to the area that is being treated on the patient. Each of conductors 202 may be in communication with one or more pickup loops 204 via one or more wires 205a-e. Also, conductors 202 may have another connection to one or more pickup loops 204 via one or more wires 206. In these instances, wire 206 may be used to create a voltage potential or voltage difference on conductors 202. Also, wire 206 may be connected to a ground potential (either separately or grounded to the patient under treatment) to create the voltage difference. The voltage potential created on each of conductors 202 creates a desired electric field. Although just one wire 206 is shown in FIG. 2 for the purpose of clarity, it should be appreciated that each of conductors 202 may have a similar voltage reference connection attached thereto.

Pickup loop 204 may be any conductive material having any particular shape (e.g., straight wire, looped coil, etc.). Also, wires 205a-e may be any conductive material capable of carrying an electrical signal from pickup loop 204 to conductors 202. Pickup loop 204 and wires 205 may be an integrated part of flexible circuit pad 106. Also, pickup loop 204 and wires 205 may be individual components independent of flexible circuit pad 106 that may be moved in various treatment locations during operation.

As discussed with reference to FIG. 1, a current (I) is applied to a magnetic stimulation device (not shown) to produce a pulsed magnetic field (having a flux density B) that is designed to provide medical treatment (e.g., TMS) to a patient. In operation, pickup loop 204 may be placed anywhere within or in close proximity to the pulsed magnetic field or in a similar magnetic field that is proportional to the therapeutic field. The therapeutic field induces an electric field (E1) in the surface tissue whose lines of flux are shown as 203a-f. This electric field, E1, is proportional to dB/dt. The magnetic field flux lines (B) are orthogonal to these electric field lines.

The pickup loop may be connected via conductors 205 directly (or indirectly) between an electrode (202a-e) and a ground reference point or a second electrode. As the magnetic field crosses pickup loop 204, a current is generated in pickup loop 204 and a voltage may be established between the connected electrodes that is generally proportional to −dB/dt and −dI/dt over certain regions near the electrodes. This voltage creates a proportionate electric field (E2) in the surface tissue between the electrodes. Since this applied electric field (E2) may be designed to be inversely proportional to the induced electric field (E1), there is subtraction wherever the fields superimpose which results in the desired reduction of discomfort.

In order to effectively distribute the canceling electric field (E2) multiple electrodes may be used. In this case, the voltage generated by pickup loop 204, which is proportional to the magnetic field created by the magnetic stimulation device, may be provided to each of conductors 202 via wires 205. As a result, voltages may be established between the several conductors 202 and creating corresponding electric fields between each of conductors 202. The electric fields created by conductors 202 are designed such that the undesired stimulation of the patient (e.g., in the scalp) is reduced, but the desired stimulation (e.g., in the brain) created by the magnetic stimulation device's magnetic field is not compromised. For example, in the context of transcranial magnetic stimulation, the electric fields created by conductors 202 may operate to reduce the impact of the magnetic stimulation device's magnetic field close to the surface of the scalp, while allowing the electromagnet's magnetic fields to penetrate deeper within the head and desirably stimulate the brain.

The desired strength and location of the fields created by conductors 202 may be varied depending on the characteristics of the patient and of system 200, as previously discussed. Although not exclusive of the techniques for varying the strength and location of the electric fields created by conductors 202, the electric fields may be varied by modifying the number of turns, the cross-sectional area of pickup loop 204, or by interposing an amplification device (e.g., transformer) between the pickup loop and the electrodes as described by System 300, FIG. 3. Another technique for varying the electric field strength created by conductors 202 includes using more than one pickup loop and varying the location of pickup loop(s) with respect to the magnetic field.

By sensing the strength of the magnetic field created by the magnetic stimulation device, pickup loop 204 may create fields (via communication with conductors 202) that are able to eliminate or reduce undesired effects of the magnetic stimulation device, while permitting the desired therapeutic effect of magnetic stimulation device (e.g., TMS). The precise size and location of the fields created by conductors 202 may be determined by vectorally adding, as is well known to those skilled in the art, the corresponding fields created by conductors 202 and by the magnetic stimulation device.

Figure 2A:
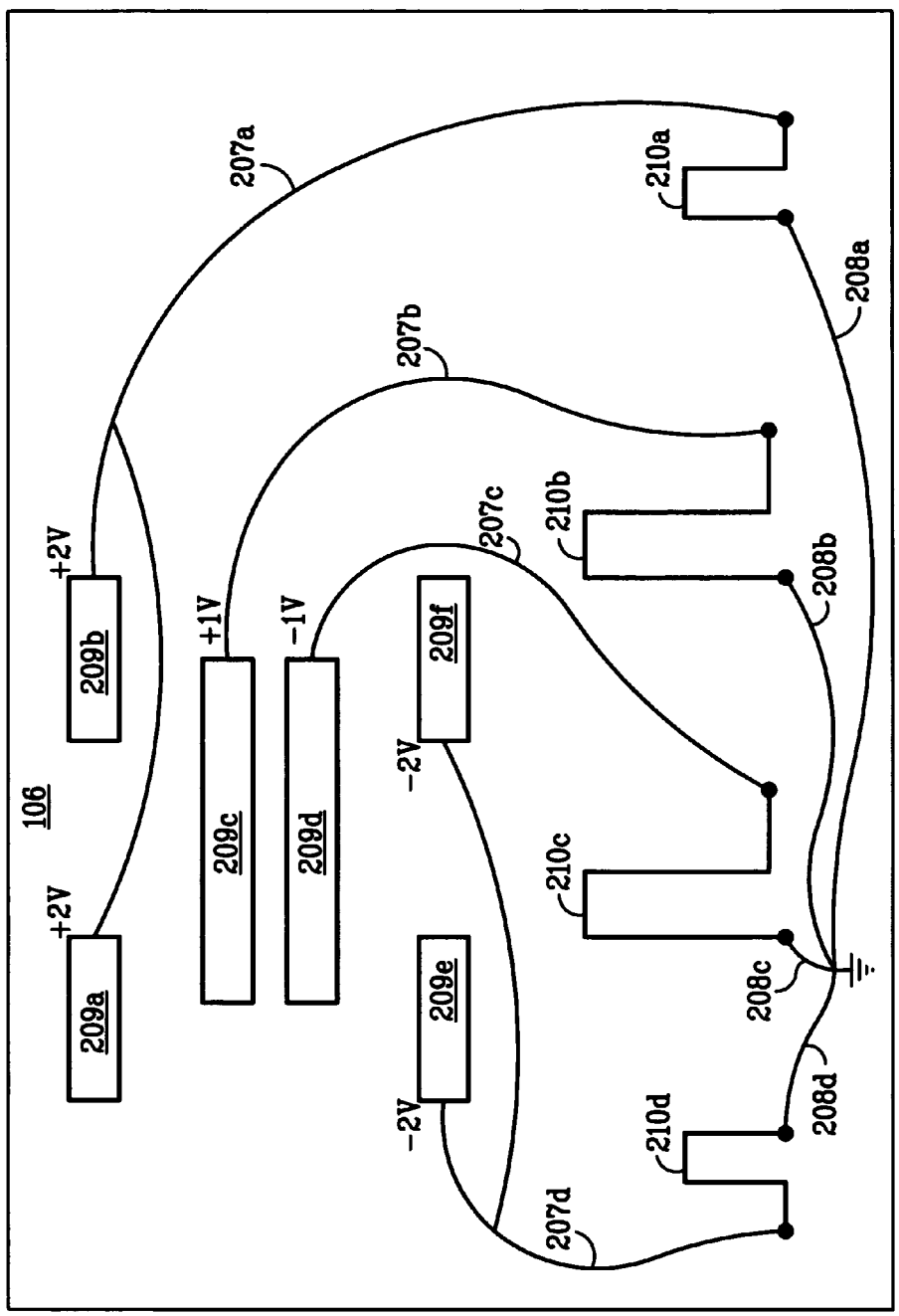
FIG. 2A is a block diagram illustrating another technique for reducing discomfort caused by transcutaneous stimulation.

FIG. 2A is a block diagram illustrating another technique for reducing discomfort caused by electrical stimulation. Specifically, FIG. 2A shows another configuration of pickup coils and conductor placement, as compared to that shown in FIG. 2. As shown in FIG. 2A, conductors 209a-f are distributed on flexible circuit pad 106. Conductors 209 also are in communication with pickup coils 210a-d. Wires 207a-d are connected from conductor 209 to pickup coils 210a-d, respectively. Also, pickup coils 210a-d are connected to a voltage reference point (e.g., ground reference) via wires 208a-d, respectively. The voltage reference may be separately provided, provided as part of the flexible circuit pad and/or be provided via attachment to the patient under treatment.

In operation, each of pickup coils 210 provides a certain predetermined voltage value to each of its respective conductors 209. The precise voltage value provided by pickup coils 210 to conductors 209 may be based on the electric and/or magnetic field that is desired to be created by each of conductors 209 to offset the undesirable effects of the magnetic stimulation device (not shown). The design of the voltage value may be made to vary depending on the size and construction of conductors 209, as well as the size and construction of pickup coils 210. For example, possible voltage values are indicated in FIG. 2A. These voltage values are merely provided for the purpose of example and to provide further the explanation.

In just one embodiment, for example, pickup coil 210d may provide −2 volts to each of conductors 209e and 209f. Also, pickup coil 210c may provide −1 volt to conductor 209, while pickup coil 210b provides +1 volt to conductor 209c. Conductors 209a and 209b may each receive +2 volts from pickup coil 210a. The voltage values and the polarity of the voltage may be based on the electric and/or magnetic field that is desired to be created on each of conductors 209. For example, a higher voltage value (e.g., 5 volts) may be applied to conductors 209c and 209d in recognition that greater undesirable field strengths are created by the magnetic stimulation device at that location. Also, by establishing a similar voltage but different polarity conductors may work in tandem (e.g., 209a and b, 209c and d, and 209e and f) to create the desired fields.

Although not shown in FIG. 2A, it should be appreciated that a voltage potential may be created individually on each of conductors 209. In particular, a voltage potential (e.g., ground potential) may created on one or more conductors 209 to generate a desired field. Also, it should be appreciated that the number of coils 210 and conductors 209 may vary depending upon the particular application.

Figure 3:
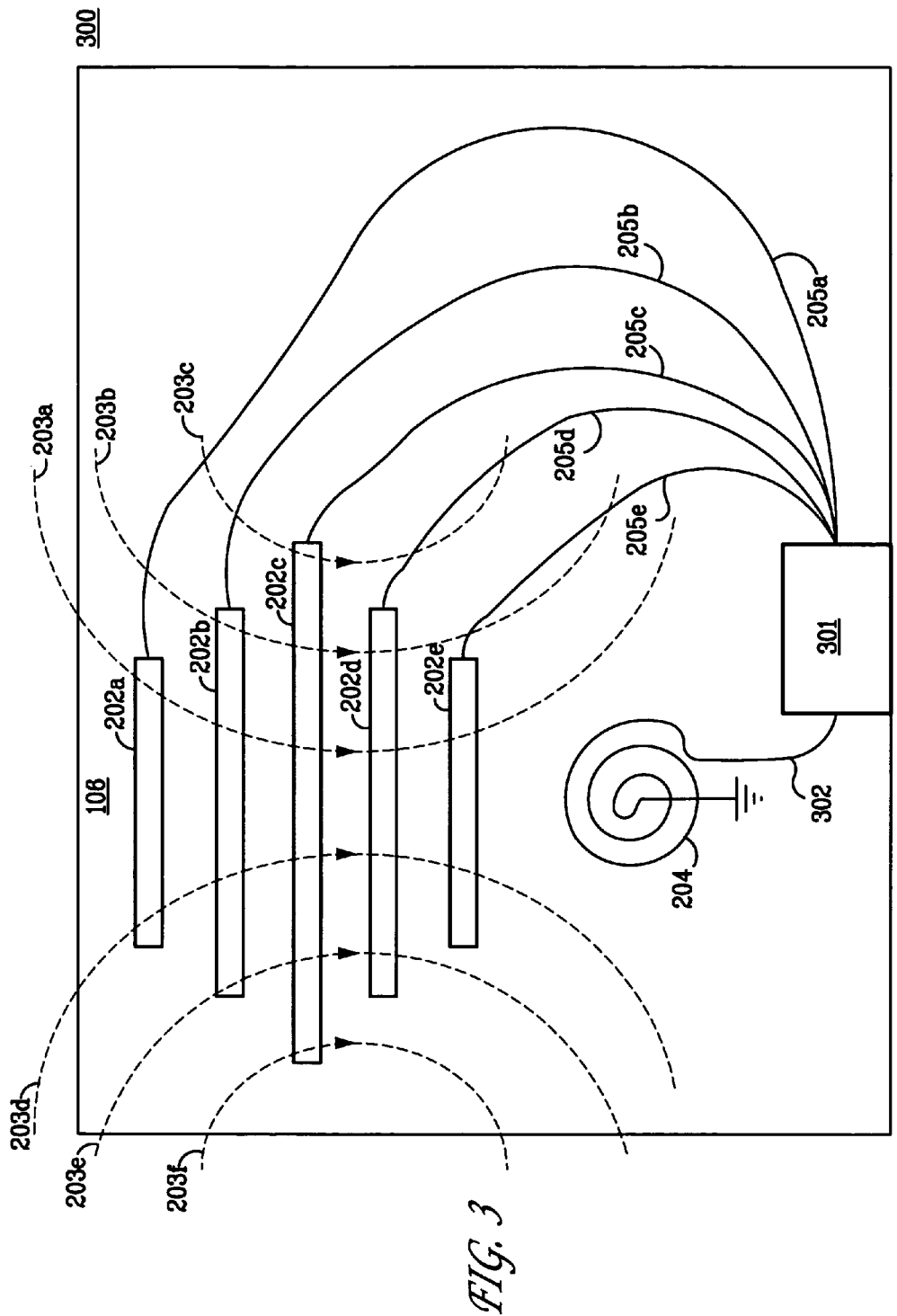
FIG. 3 is a block diagram illustrating another technique for reducing discomfort caused by transcutaneous stimulation.

FIG. 3 is a block diagram illustrating another technique for reducing discomfort caused by electrical stimulation. As shown in FIG. 3, a system 300 is similar to system 200, discussed with reference to FIG. 2. In addition to the components shown in system 200, system 300 also includes a signal processor 301 in communication with pickup loop 204 via wire 302. As with signal processor 104, discussed with reference to FIG. 1, signal processor 301 may operate to manipulate the electrical voltage and/or current induced on pickup loop 204 and provided to conductors 202. In particular, depending on the characteristics of system 300, signal processor 301 may be designed to scale the induced voltage and/or current signal up and/or down to a level that permits conductors 205 to create a magnetic field sufficient to reduce the discomfort caused by the magnetic stimulation device (not shown) on the patient, without reducing its therapeutic effects.

The design and output of signal processor 301 may be used in lieu of or in combination with the modifications used to vary the electric fields created by conductors 202, as discussed with reference to FIG. 2 with regard to the characteristics of pickup loop 204. An amplifier (not shown), similar to amplifier 103 discussed with reference to FIG. 1 may be designed to amplify the induced voltage signal up and/or down in combination with signal processor 301. Also, system 300 may include any combination of varying the above-mentioned characteristics to allow conductors 202 to produce electric fields that have proper characteristics to reduce discomfort created by therapeutic electrical stimulation. For example, having the flexibility to vary the signal from pickup loop 204 using signal processor 301 may allow less stringent design criteria restrictions for the construction and placement of conductors 202, and thus further facilitate on-site implementation.

Also, it should be appreciated that signal processor 301 may be designed to allow different voltage and/or current signal strengths to be applied individually to each of conductors 202. This variable conductor signal may be desirable in certain configurations. For example, as shown in FIG. 3, electric field lines 203a and 203d converge as they approach the center of flexible circuit pad 106. Because it is well known to those skilled in the art that field lines 203a and 203d may vectorally add in this location, resulting in a greater electric field strength (created by the magnetic stimulation device) at this location than at other locations in system 300.

In the context of rTMS and/or TMS, this greater electric field strength beneficially may result in ideal stimulation of the brain for the treatment of depression, for example. At the same time, this greater electric field strength also undesirably may result in creating greater discomfort in the non-brain tissue, muscle and/or nerves, or other parts of the brain that do not need to be stimulated. Therefore, in order to offset the undesirable effect where electric field lines 203a and 203d are stronger, signal processor 301 may apply a larger voltage and/or current signal to a conductor located in this location than to other conductors. For example, conductor 202c may receive a greater voltage and/or current signal than the other conductors because it is located in the area where electric field lines 203a and 203d are stronger. Therefore, signal processor 301 may permit conductor 202c to create a relatively greater electric field as compared to the other conductors.

Although the discussion of the ability of signal processor 301 to vary the current and/or voltage signal provided to each of conductors 202 has been discussed in the context of field strength, this example is not exclusive. It should be appreciated that other factors may drive the decision to provide different signals to each of conductors 202. For example, the anatomy or sensitivity of the part of the patient that is being treated with respect to the arrangement of the conductors on flexible circuit pad 106 may result in signal processor 301 providing a relatively greater and/or lesser current to conductor 202a than the other conductors. Also, as another example, the lines of flux created by the main electromagnet device may be different than as illustrated in FIG. 3 and thus the design of signal processor 301 may be such that greater current and/or voltage signal may be provided to other of conductors 202. Therefore, it should be appreciated that the discussion is not meant to be limited to any of the above examples, which simply are provided for the purpose of clarity and explanation.

Figure 4:
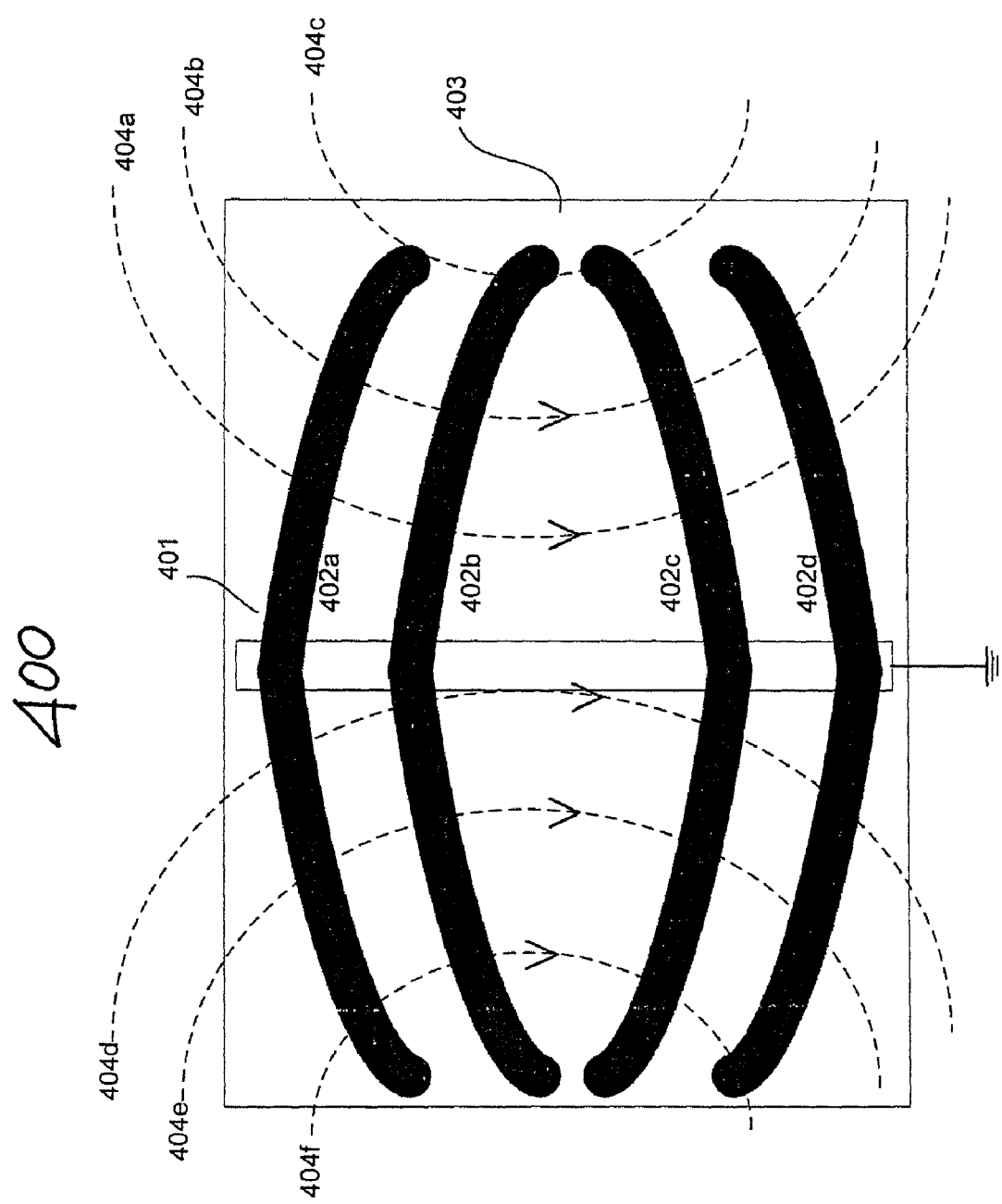
FIG. 4 is a block diagram illustrating another technique for reducing discomfort caused by transcutaneous stimulation.

FIG. 4 is a block diagram illustrating another technique for reducing discomfort caused by electrical stimulation. As shown in FIG. 4, a system 400 includes a flexible circuit pad 401 having conductors 402a-d. Although conductors 402 are shown centered and evenly spaced on flexible circuit pad 401, it should be appreciated that conductors may be any size or shape, arranged in any configuration, and placed on any location on flexible circuit pad 401. Also, although conductors 402 are illustrated as having an arc shape, it should be appreciated that the invention is not limited to any particularly shaped conductors. For example, conductors 402 may have any shape, including the shapes depicted in FIGS. 1-3, circular coil shapes, etc. Conductors 402 also are connected to a common connector 403. Common connector 403 may provide a referenced voltage level, like a ground voltage level, for example. Also, as previously discussed, the magnetic stimulation device (not shown) creates magnetic flux lines 404a-f.

In operation, system 400 uses shielding techniques to reduce and/or to redistribute the electric field effects of fields 404a-f created by the magnetic stimulation device and used for therapeutic purposes (e.g., rTMS and TMS). In particular, as previously discussed, magnetic flux lines 404 create electric fields which induce electrical currents in the nerves, muscle and tissue of the patient. Certain of these nerves, muscle and tissue may be desirably stimulated by the induced current (e.g., the brain in rTMS and TMS). However, certain of other nerves, muscle and tissue (e.g., the scalp in rTMS and TMS) may be undesirably stimulated by the induced current created by the magnetic stimulation device.

Conductors 402 operate to disrupt the flow of current in the patient's surface tissue so that system 400 may permit the desirable stimulation of certain parts of the patient's anatomy, while reducing or eliminating the undesirable stimulation of other parts of the patient. In particular, conductors 402 may be designed with certain physical and/or electrical characteristics such that they offer a path of lesser resistance for the induced current than the portion of the patient in which the undesired induced current would flow. As a result, conductors 402 operate to reduce or eliminate the undesired current induced a certain portion of the patient, while still permitting the desired current to be induced in another portion of the patient.

The characteristics of conductors 402 may be designed to provide the path of lesser resistance based upon a number of factors and variables. For example, increasing the conductivity of conductors 402 may be accomplished by varying the physical and/or electrical characteristics of conductors 402 as compared to the particular portion of the patient that is being treated. Also, the shape and configuration of conductors 402 relative to the direction and strength of magnetic fields 404a-f may be varied (e.g., conductors 402 may be curved as illustrated in FIG. 4) to allow conductors 402 to provide a larger conductive path of lesser resistance. In addition, conductors 402 may be configured and shaped (e.g., curved) to allow the conductors to be in a substantially perpendicular arrangement with respect to electric field lines 404a-f in order to "intercept" more of the current caused by the induced electric field, conduct the intercepted current to a more acceptable location, and redistribute the current back to the surface-proximate tissue in a manner that minimizes sensation. Although determining the configuration and shape of conductors 402 may be necessary in properly reducing or eliminate the undesired induced current on the patient, it should be appreciated that the invention is not limited to any particular shape or configuration of the conductors, but include all possible shapes and configurations.

In the context of rTMS and TMS, conductors 402 may have electrical and physical characteristics to redirect the flow of current away from the tissue, nerve, and muscle found closer to the surface of the head or scalp. One way of accomplishing this may be by determining the typical or specific electrical conductivity of the surface-proximate tissue, nerve, and muscle, and designing conductors 402 to have an equal or greater conductivity, as necessary. Also, the electrical and physical characteristics of conductors 402 may be designed to redirect current that may stimulate the surface-proximate tissue, nerve, and muscle without significantly interfering with the therapeutic current desirably induced on the brain tissue under treatment.

Although conductors 402 are shown connected to common connector 403, it should be appreciated that any one or more of conductors 402 may operate independently of the others, or that just one conductor may be used. For example, in the context of rTMS and TMS, it is well known to those skilled in the art that the trigeminal nerve is particularly sensitive to electrical stimulation as compared to other prefrontal areas of the scalp. Therefore, one or more conductors 402 may operate together or independently in close proximity to the trigeminal nerve to redirect any nearby electric fields. Also, certain conductors 402 may be dedicated to protecting the trigeminal nerve specifically. In addition, in the context of the trigeminal nerve, in just one embodiment, the conductor or conductors 402 may be positioned directly over the trigeminal nerve and attached directly to the patient in a direction consistent with the direction of the nerve. In this way, the arrangement, positioning and configuration of the conductor or conductors may be customized to locally protect a particular tissue, muscle or nerve, like the trigeminal nerve. Although the discussion has focused on protecting of the trigeminal nerve, it should be appreciated that one or more conductors may be placed over any part of the patient that may be more or less sensitive or that simply is desired to be protected. In addition, it should be appreciated that placing one or more conductors on the patient may be used in combination with any of the other techniques described with reference to FIGS. 1-3.

Figure 5:
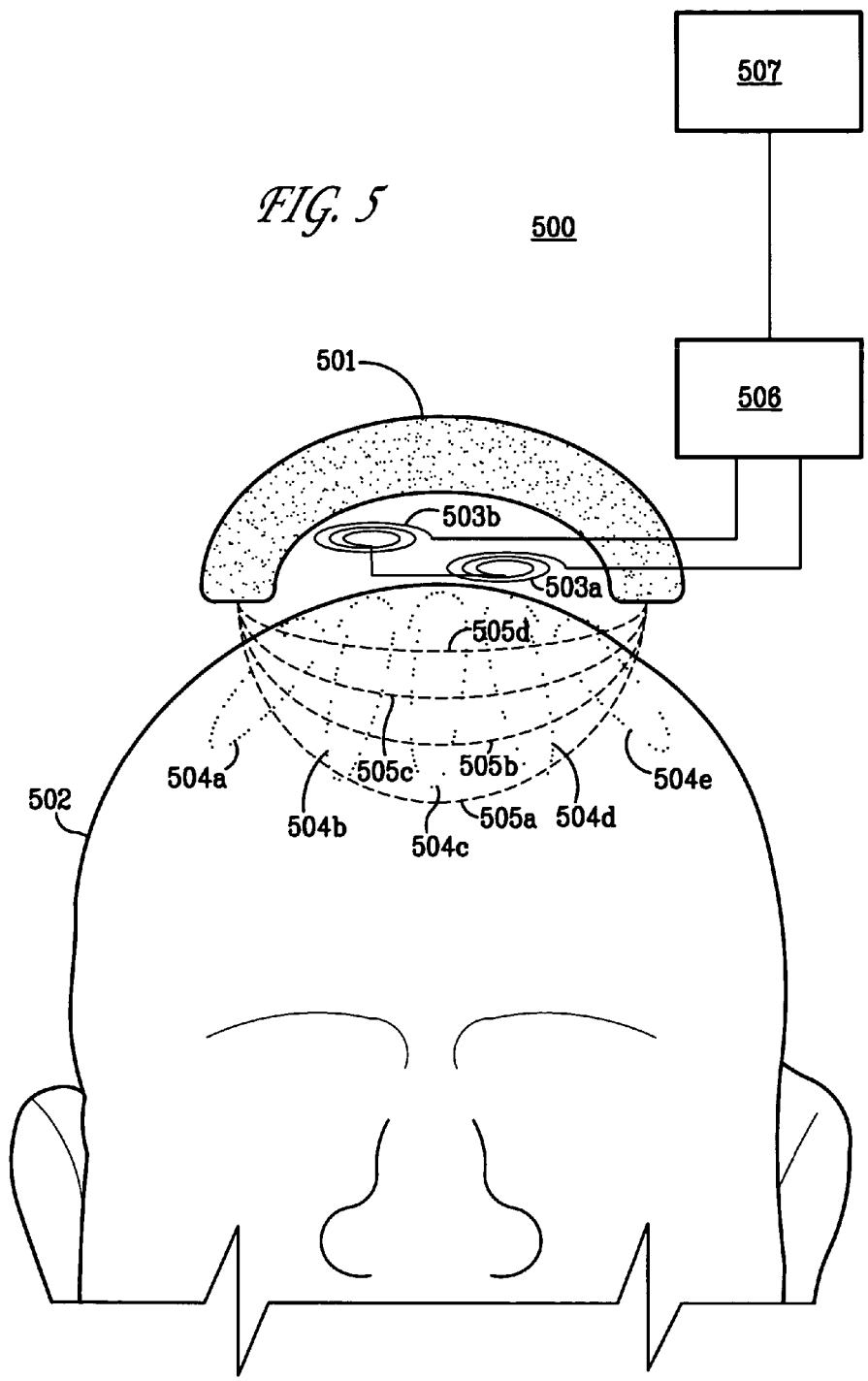
FIG. 5 is a block diagram illustrating another technique for reducing discomfort caused by transcutaneous stimulation.

FIG. 5 is a block diagram illustrating another technique for reducing discomfort caused by electrical stimulation. As shown in FIG. 5, a system 500 includes conductive coils 503a and 503b located above a patient's head 502 and under a magnetic stimulation device 501 (e.g., magnet with ferromagnetic core). Also, conductive coils 503a and 503b are in communication with a signal processor 506, which receives electrical power from a power source 507. Although the arrangement of magnetic stimulation device 501 and conductive coils 503a and 503b are illustrated in FIG. 5 in a certain configuration with respect to the patient's head 502, it should be appreciated that this configuration is not meant to be exclusive, but simply provide one example for the purposes of clarity and explanation. For example, conductive coils 503a and 503b may be in direct or indirect contact with either the patient's head 502 and/or magnetic stimulation device 501. Furthermore, conductive coils 503a and 503b may be located other than in between the patient's head 502 and magnetic stimulation device 501. Also, although magnetic stimulation device 501 is shown as a magnet having an arc-shaped ferromagnetic core, it should be appreciated that it may include any device capable of creating magnetic stimulation.

When an electric voltage and/or current is applied to magnetic stimulation device 501, a magnetic field having magnetic flux lines 505a-d is created between the poles of magnetic stimulation device 501. The pulsed magnetic field created by magnetic stimulation device 501 and having magnetic flux lines 505*a-d* also create an electric field represented by 504*a-e*. Of course, as with FIGS. 1-4 the depiction of magnetic flux lines 505*a-d* and electric field 504*a-e* are merely representative of such properties simply for the purpose of a discussion in the context of the invention.

As shown in FIG. 5, electric fields 504*a-e* become dispersed as they move away from magnetic stimulation device 501. Yet, at the top of the patient's head 502 (or perhaps in another location depending on the location and configuration of the magnetic stimulation device) located between the poles of magnetic stimulation device 501, the electric field lines 504*a-e* are located closer to one another. Also, well known to those skilled in the art, the strength of the electric field decreases as a square of the distance away from the source of the electric field. These two well-known properties of electric fields create a relatively stronger electric field presence at the top of the patient's head 502 and between the poles of magnetic stimulation device 501. As a result, this relatively stronger electric field in turn induces a relatively larger current in the surface-proximate tissue, muscle and nerves located at the top of the patient's head 502. In some instances, this relatively larger current may cause greater discomfort to certain portions of the patient's anatomy (e.g., the scalp). System 500 uses conductive coils 503*a* and 503*b* to help alleviate the patient's discomfort.

Conductive coils 503*a* and 503*b* receive electrical power from power source 507 via signal processor 506. When conductive coils 503*a* and 503*b* receive electrical energy another magnetic field (B2, not shown) is created by conductive coils 503*a* and 503*b*. The magnetic field (B2) created by conductive coil (in cooperation with power source 507 and signal processor 506) may be designed to reduce, eliminate or counteract the magnetic lines of flux 504*a-e*, so as to eliminate discomfort caused by the current induced in a portion of the patient's head 502 by electric field 504*a-e* and magnetic lines of flux 505*a-d*. The location, size and strength of conductive coil's 503 magnetic field (B2) required to sufficiently offset the surface effect of the magnetic field (B) created by magnetic stimulation device 501 may vary with the particular circumstances and construction of system 500. For example, the necessary offsetting magnetic field (B2) created by conductive coils 503*a* and 503*b* may vary with the patient, the construction and location of magnetic stimulation device 501, the size and construction of conductive coils 503*a* and 503*b*, and other variable circumstances. Also, conductive coils 503*a* and 503*b* may be wound in a direction opposite of main magnetic stimulation device.

There are numerous methods and techniques available to accommodate the variation necessary in system 500 to sufficiently offset the undesirable effect of the fields created by magnetic stimulation device 501. For example, signal processor 506 may receive a feedback signal (not shown) from magnetic stimulation device 501 and/or its electric or magnetic fields so as to create a properly sized magnetic field from conductive coils 503*a* and 503*b*. This feedback may be provided via a direct connection to magnetic stimulation device 501 or by receiving a current supplied to magnetic stimulation device 501. Using this input, signal processor 506 may vary the level of power provided to conductive coils 503*a* and 503*b* and thus vary its resulting and offsetting fields. An alternative arrangement is to permit the operator to manually adjust current levels to coils 503*a* and 503*b* based on patient feedback, based on other signal feedback, or arbitrarily.

Also, the arrangement, location and configuration of may be varied depending on the particular circumstances. For example, the number of turns or loops in conductive coils 503*a* and 503*b* may be varied based on the output of magnetic stimulation device 501. Also, as depicted in FIG. 5, a plane of conductive coils 503*a* and 503*b* may be orthogonal to the magnetic field created by the magnetic stimulation device 501 and/or to magnetic stimulation device 501 itself. In addition, conductive coils 503*a* and 503*b* may be designed to have a certain cross-sectional area and/or aspect ratio.

Also, although signal processor 506 and power source 507 are shown, the size and construction of conductive coils 503*a* and 503*b* may be designed such that the desired strength of the magnetic field is created by conductive coils 503*a* and 503*b* itself. This design may be based on the electrical properties of conductive coils 503*a* and 503*b*, such as conductivity, field saturation level, influence of magnetic flux lines 504*a-e* on conductive coils 503*a* and 503*b*, and undesirable heat generating properties of conductive coils 503*a* and 503*b*, etc. The conductive coils may have air cores, or ferromagnetic cores of materials such as 3% silicon steel or vanadium permandur. These are just examples of possible materials that may be used to create conductive coils 503*a* and 503*b*.

It should be appreciated that the described techniques for arriving at the correct offsetting magnetic field created by conductive coils 503*a* and 503*b* may be accomplished via a combination of these or any other techniques. Also, it should be appreciated that the size and location of the countervailing magnetic field created by conductive coils 503*a* and 503*b* may be such that the discomfort causing effect on surface-proximate tissue, muscles and nerves are reduced, while the therapeutic effect of magnetic lines of flux 505*a-d* on deeper elements (e.g., the brain) are not adversely effected. For example, the geometry of conductive coils 503*a* and 503*b* may be varied such that its magnetic fields do not deeply penetrate the patient (e.g., air core coil). As another example, the current provided to conductive coils 503*a* and 503*b* may be minimized so as to produce relatively weaker magnetic fields.

It also should be appreciated that conductive coils 503*a* and 503*b* may be one of an array of coils. In this example, each of the coils may have similar or different physical and electrical characteristics depending upon the portion of magnetic stimulation device's 501 magnetic field that it is designed to be operated upon. In addition, each coil of such an array may have a separately adjustable current drive level that is set by the signal processor 506 based on preset values, empirically determined values, sensed feedback, patient feedback to the operator, or independent manual setting by the operator.

The coils may be attached directly or indirectly to the patient's head 502 and/or attached directly or indirectly to magnetic stimulation device 501. System 500 also may use shielding techniques to block or reduce the magnetic fields generated by conductive coils 503*a* and 503*b* from adversely effecting the operation of ferromagnetic core 501, or to minimize coupling of the stimulator field (B) with the conductive coils. For example, system 500 may include a magnetic shield (not shown) placed in some location proximate and/or between conductive coils 503*a* and 503*b* and magnetic stimulation device 501, so as to reduce or eliminate the magnetic field between conductive coils 503*a* and 503*b* and the magnetic stimulation device 501. Such magnetic shields may be fabricated from ferrite materials, as an example.

The components shown in FIG. 5 are not exclusive but are provided simply for the purposes of explanation. Other components may be desirable, as well. For example, communication between conductive coils 503*a* and 503*b* may pass through a shunting device, so as to eliminate any undesirable conduction of energy back into signal processor 506.

Figure 6:
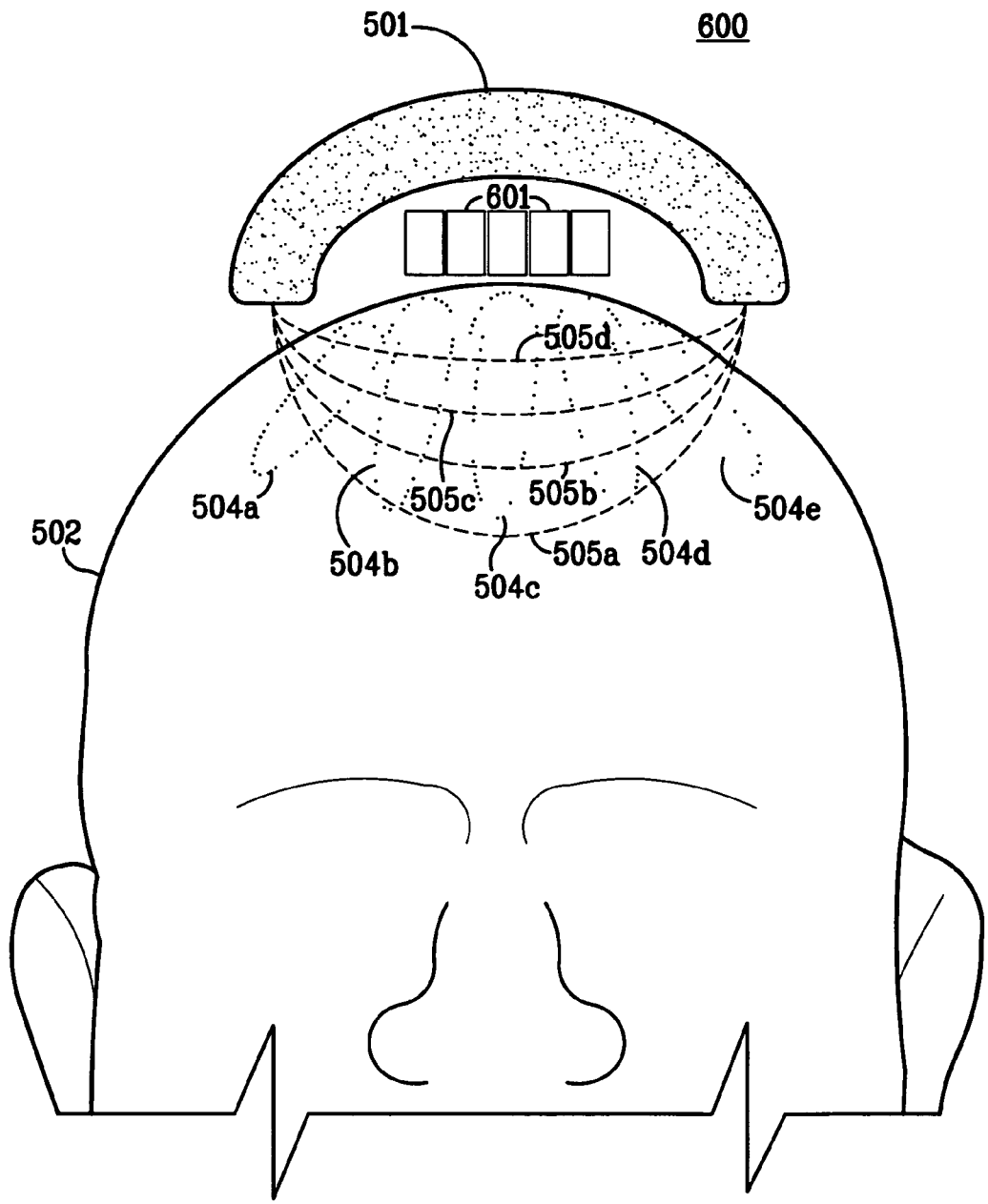
FIG. 6 is a block diagram illustrating another technique for reducing discomfort caused by transcutaneous stimulation.

FIG. 6 is a block diagram illustrating another technique for reducing discomfort caused by electrical stimulation. As shown in FIG. 6, a system 600 includes one or more ferrite pads 601 located above a patient's head 502 and under a magnetic stimulation device 501. It should be appreciated that the physical configuration of ferrite pads 601 are illustrated for the purpose of discussion and clarity, and is not meant to be an exclusive representation of such a configuration. For example, as with conductive coils 503a and 503b discussed with reference to FIG. 5, ferrite pads 601 may be located between magnetic stimulation device 501 and the patient's head 502. Also, as discussed, ferrite pads 601 may be attached directly and/or indirectly to the patient's head 502 and/or directly or indirectly connected to magnetic stimulation device 501. In addition, the number and placement of ferrite pads 601 are not limited to any particular configuration, and may be used in conjunction with any of the other methods described herein.

Ferrite pads 601 operate to effectively "absorb" the magnetic field and magnetic flux lines 504a-e created by magnetic stimulation device 501. In particular, ferrite pads 601 may be designed and constructed to offset, reduce and/or absorb the magnetic flux lines 504a-e that stimulate the surface-proximate tissue, while permitting those magnetic flux lines that penetrate deeper into the patient for therapeutic purposes to pass substantially unaffected. Also, by using a ferrite material, ferrite pads 601 typically have low conductivity and therefore do not encourage induced eddy currents and associated heating or temporal disruption of the therapeutic magnetic field created by magnetic stimulation device 501. It should be appreciated that although system 600 has been described in the context of ferrite material, the pads also may be made of other non-ferrite material and/or a combination of ferrite material and non-ferrite materials.

The components shown in FIG. 6 are not exclusive but are provided simply for the purposes of explanation. Other components may be desirable, as well. For example, in response to the magnetic field from the magnetic stimulation device 501, ferrite pads 601 may create fields that undesirably are directed toward magnetic stimulation device 501. Such undesirable fields may effect the operation and/or efficiency of magnetic stimulation device 501. For example, such fields may cause magnetic stimulation device 501 to saturate at a different level than expected. Therefore, other components may be used to block or attenuate the fields from ferrite pads 601 to magnetic stimulation device 501. Such blocking techniques may be designed to be unilateral or substantially unilateral to permit the fields to pass from magnetic stimulation device 501 to ferrite pads 601, but to interrupt the fields from ferrite pads to magnetic stimulation device 501.

Figure 25:
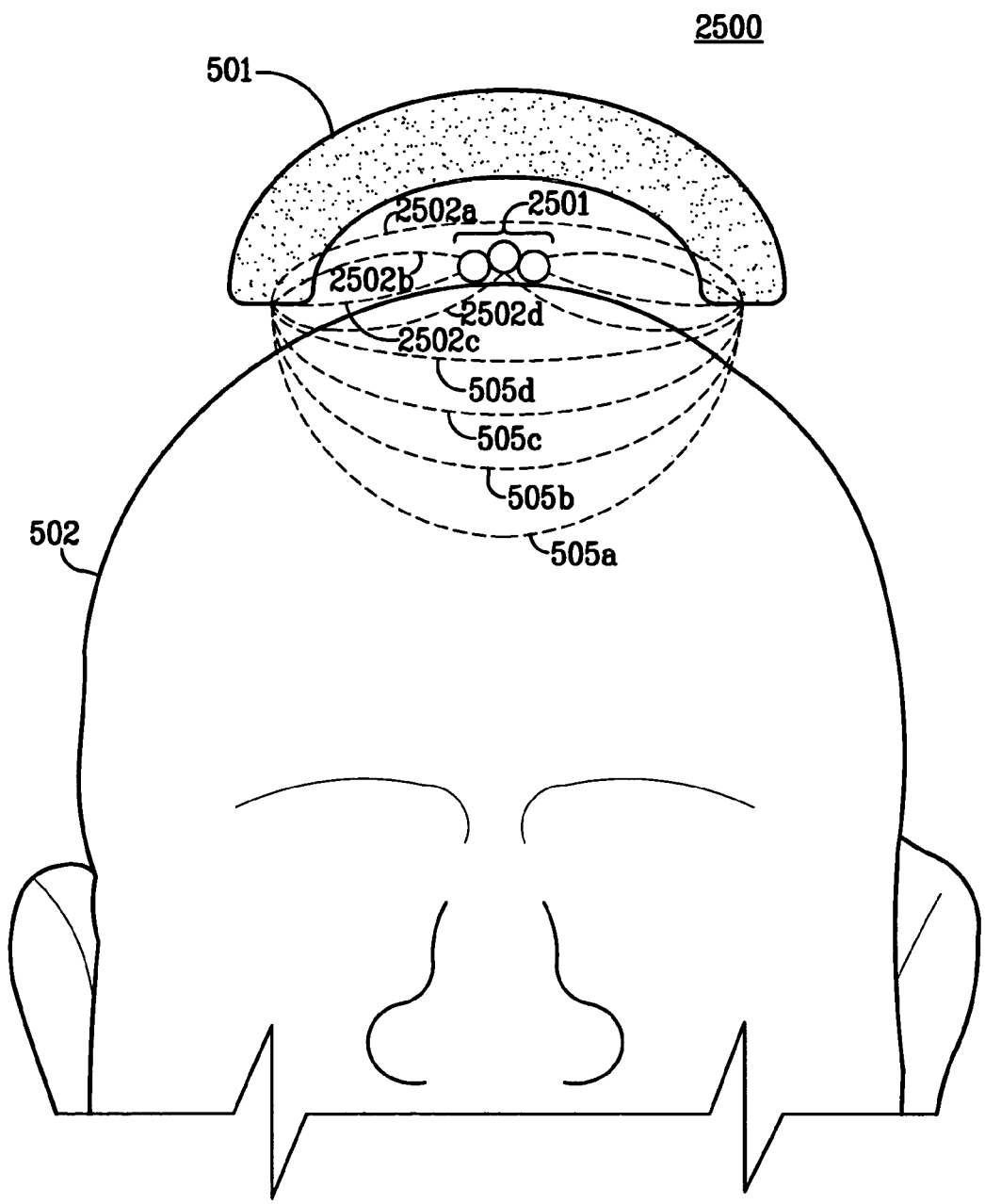
FIG. 25 is a block diagram illustrating another technique for reducing discomfort caused by electrical stimulation.

FIG. 25 is a block diagram illustrating another technique for reducing discomfort caused by electrical stimulation. As shown in FIG. 25, a system 2500 includes one or more magnetic materials 2501 located above a patient's head 502 and under a magnetic stimulation device 501. It should be appreciated that the physical configuration of magnetic materials 2501 are illustrated for the purpose of discussion and clarity, and is not meant to be an exclusive representation of such a configuration. For example, as with conductive coils 503a and 503b discussed with reference to FIG. 5, magnetic materials 2501 may be located between magnetic stimulation device 501 and the patient's head 502. Also, as discussed, magnetic materials 2501 may be attached directly and/or indirectly to the patient's head 502 and/or directly or indirectly connected to magnetic stimulation device 501. Also, magnetic materials 2501 may be made to be a part of and/or connected to magnetic stimulation device 501. For example, magnetic stimulation device 501 may be manufactured with a certain portion having characteristics of magnetic materials 2501. The contemplated embodiments are not limited to the particular placement of magnetic materials 2501. In addition, the number and placement of magnetic materials 2501 are not limited to any particular configuration, and may be used in conjunction with any of the other methods described herein.

It also should be appreciated that magnetic materials 2501 may take a form other than illustrated in FIG. 25. For example, instead of circular magnetic materials, the material may be a continuous structure that may span any portion of the patients head and/or magnetic stimulation device 501. Such a structure may be in the form of a block and/or a sheet, for example. Also, the structure may be straight or may have curved portions to conform to the shape of the patients head. Also, the structure may have another customized shape that conforms to another part of the anatomy that may be treated. In just one embodiment, for example, the magnetic materials may include three steel wire cables having a 0.1 inch diameter and a 3 inch length. Therefore, when referring to magnetic materials 2501 in the discussion, it should be appreciated that the embodiments include all such forms, other than a wire form.

Magnetic materials 2501 operate to effectively "absorb" and/or reroute portions of the magnetic field and magnetic flux lines created by magnetic stimulation device 501. In particular, magnetic materials 2501 may be designed and constructed to offset, reduce, absorb, and/or redirect certain magnetic flux lines 2502a-d that otherwise would stimulate the surface-proximate tissue, while permitting other magnetic flux lines 505a-d to desirably penetrate deeper into the patient for therapeutic purposes to pass substantially unaffected. The precise location and placement of magnetic materials 2501 may be adjusted and/or moved depending upon the portion of the anatomy for which the flux lines should be modified. For example, in some instances it may be desirable to place magnetic materials 2501 as close as possible to the scalp. In other instances, it may be more desirable to place magnetic materials 2501 closer to magnetic stimulation device. Also, magnetic materials 2501 may be moved along the treatment area (e.g., moved further down along the scalp line) to a location that requires reduced stimulation. The precise location may be varied depending upon the measured strength of the magnetic field at particular locations of the patient's anatomy. For example, it may be desirable to place magnetic materials 2501 at the top of the patient's head to offset a stronger generated field (e.g., based on the design of the magnetic stimulation device), and perhaps, a more sensitive portion of the anatomy to the magnetic fields.

Also, magnetic materials 2501 may be made of any type of material and or composition that facilitates absorbing and/or redirecting the magnetic flux lines. For example, by using a ferrite material, magnetic materials 2501 may redirect the magnetic flux lines while allowing relatively low conductivity and therefore reducing induced eddy currents and associated heating or temporal disruption of the therapeutic magnetic field created by magnetic stimulation device 501. Also, magnetic materials 2501 may be made of a powdered iron material having a distributed gap core structure to further reduce heating concerns created by eddy currents. It should be appreciated that although system 2500 has been described in the context of ferrite material, the pads also may be made of other non-ferrite material and/or a combination of ferrite material and non-ferrite materials.

The components shown in FIG. 25 are not exclusive but are provided simply for the purposes of explanation. Other components may be desirable, as well. For example, in response to the magnetic field from the magnetic stimulation device 501, magnetic materials 2501 may create fields that undesirably are directed toward magnetic stimulation device 501. Such undesirable fields may effect the operation and/or efficiency of magnetic stimulation device 501. For example, such fields may cause magnetic stimulation device 501 to saturate at a different level than expected. Therefore, other components may be used to block or attenuate the fields from magnetic materials 2501 to magnetic stimulation device 501. Such blocking techniques may be designed to be unilateral or substantially unilateral to permit the fields to pass from magnetic stimulation device 501 to magnetic materials 2501, but to interrupt the fields from magnetic materials 2501 to magnetic stimulation device 501.

Figure 26:
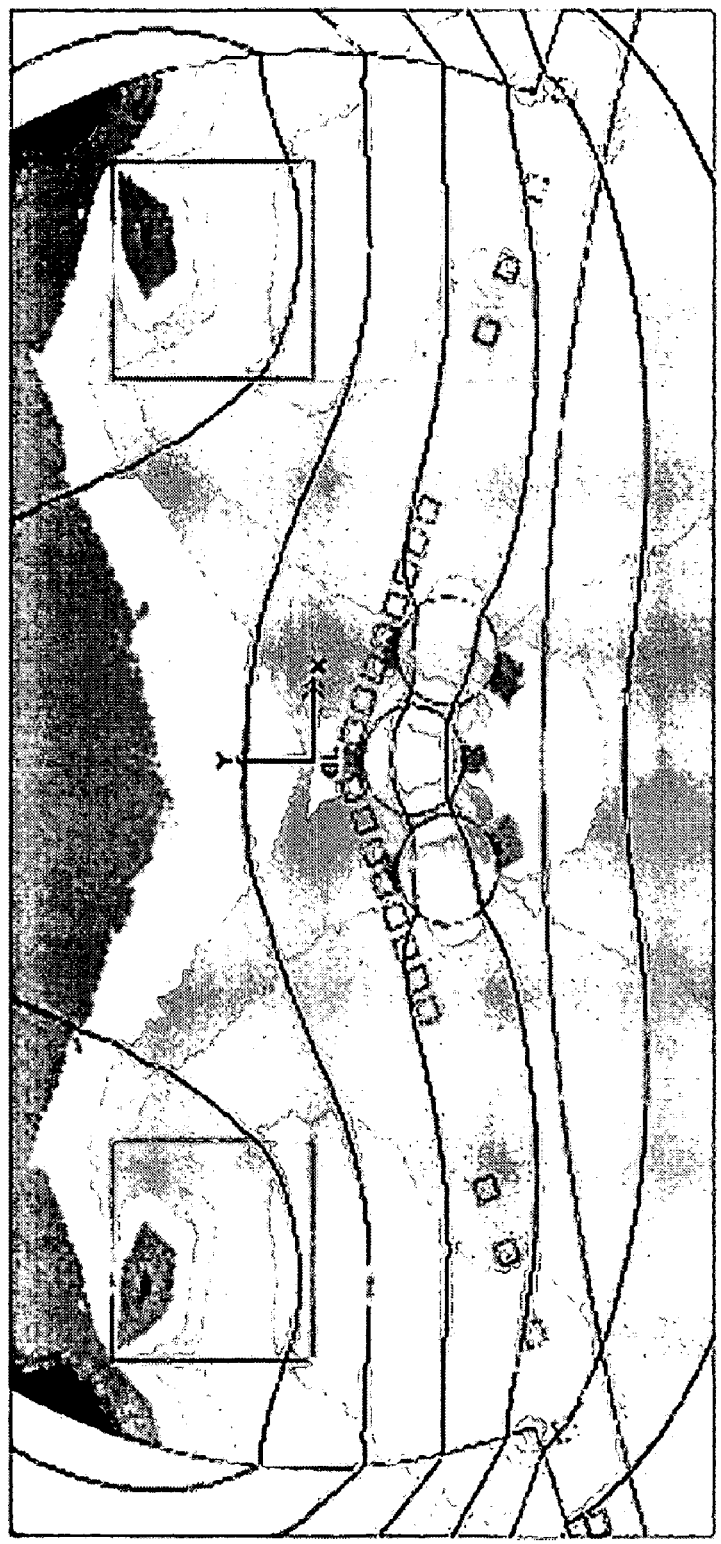
FIG. 26 provides a visual depiction of the effect of conductors on magnetic flux lines created by a magnetic stimulation device.

FIG. 26 provides a visual depiction of the effect of magnetic materials 2501 on magnetic flux lines created by magnetic stimulation device 501. As shown in FIG. 26, the magnetic flux lines that typically would travel below magnetic materials 2501, and therefore onto the scalp of the patient, are redirected toward magnetic materials 2501. As a result of the increased flux lines, the magnetic field created is greater in and around magnetic materials 2501 as depicted by the darker shaded areas. Therefore, by directing the magnetic field toward magnetic materials 2501 lesser magnetic field is directed toward the patient at the area in proximity to magnetic materials 2501.

FIG. 27 is a graphical depiction of the effect of magnetic materials 2501 on the magnetic field as a function of distance. As shown in FIG. 27, the dashed line depicts the magnetic field with the presence of magnetic materials 2501 (i.e., "shunt") and the sold line depicts the magnetic field without the presence of magnetic materials 2501 (i.e., "no shunt"). As shown, magnetic materials 2501 cause an increase or spike in the magnetic field at shorter distances (e.g., near the patient's scalp), yet leaves the magnetic field essentially unaffected at longer distances (e.g., within the skull and near the brain). From the graph it may be desirable to place the scalp at a distance represented by the portion of the graph where the dashed line falls below the solid line, indicating a desirable decrease in magnetic field.

Figure 7:
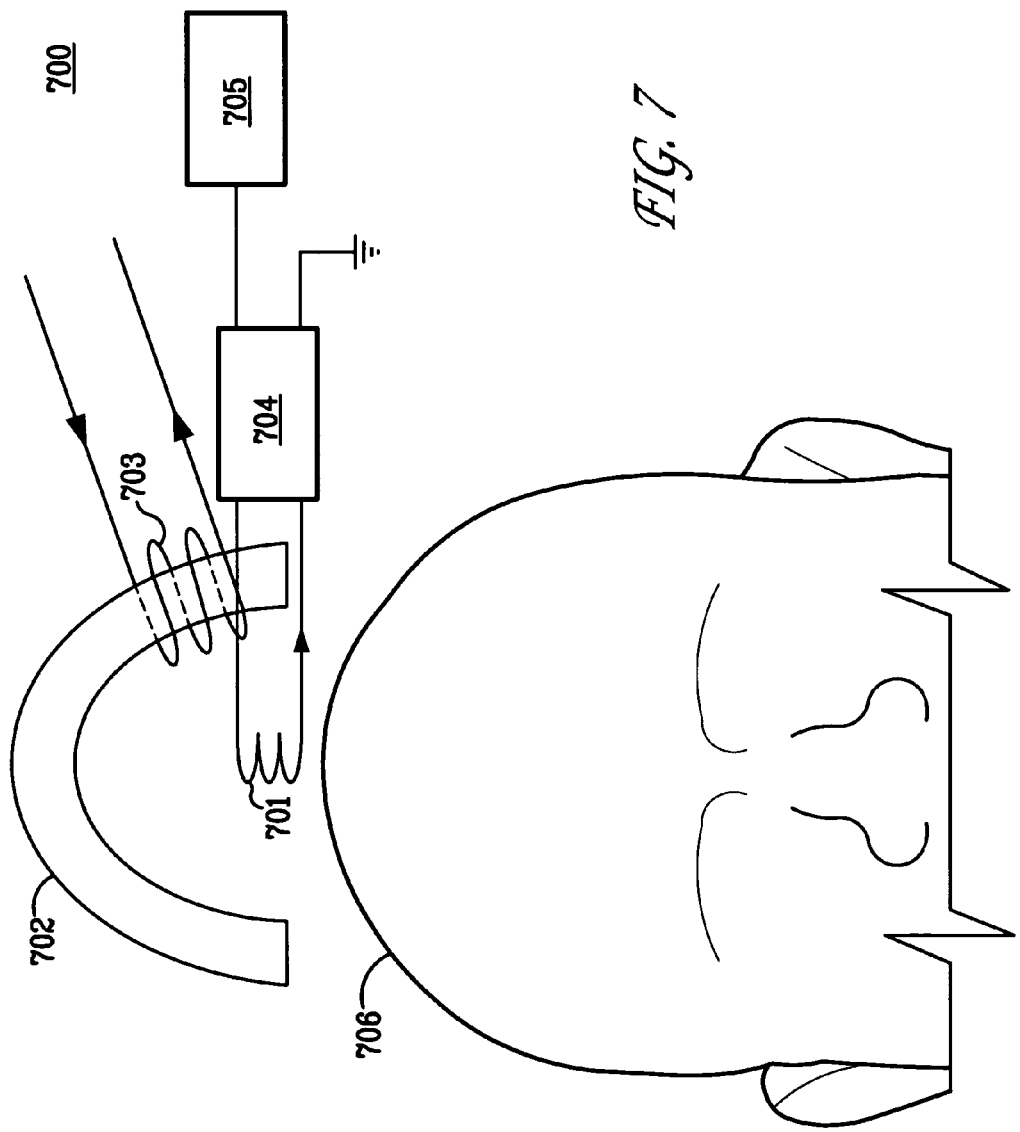
FIG. 7 is a block diagram illustrating another technique for reducing discomfort caused by transcutaneous stimulation.

FIG. 7 is a block diagram illustrating another technique for reducing discomfort caused by electrical stimulation. As shown in FIG. 7, a system 700 includes a magnetic stimulation device 702 that receives power from a stimulation circuit 703 to create magnetic fields (not shown) in the patient's head 706. As previously discussed, magnetic stimulation device 702 creates magnetic fields that induce current within the patient for certain beneficial therapeutic effects, like the treatment of depression using TMS, for example. Also, however, the same magnetic fields create discomfort for the patient by undesirably inducing current into surface-proximate tissue, nerves and muscle.

A surface coil 701, located at or near the patient (and possibly between the patient and magnetic stimulation device 702), may be used to offset, eliminate or reduce the undesired effects of the magnetic fields created by magnetic stimulation device 702. In particular, surface coil 701 may generate its own magnetic field(s) that offset the portion of the magnetic fields created by magnetic stimulation device 702 that act to undesirably stimulate surface-proximate tissue, nerves and muscle. Also, the values of the magnetic fields created by surface coil 701 may be such that the magnetic fields created by magnetic stimulation device 702 having therapeutic value continued to be passed to the patient without substantial interference.

The strength and timing of the magnetic fields, for example, created by surface coil 701 may be generated using a number of techniques. These techniques are similar to the example discussed with reference to FIGS. 1-4. Although these techniques will be discussed, it should be appreciated that these examples are provide for the purpose of clarity and further explanation, but are not meant to provide exclusive examples as contemplated by the invention.

In one embodiment, for example, power source 705 provides power to signal generator 704. Signal generator 704 then passes a signal (e.g., current and/or voltage signal) to surface coil 701 to create a magnetic field from surface coil 701. The required strength and location of the magnetic field from surface coil 701 may be varied by signal generator 704 or by power source 705. Signal generator 704 also may apply the timing necessary to synchronize the firing of the fields created by surface coil 701 with the firing of the fields created by magnetic stimulation device 702. Also, the physical and electrical characteristics of surface coil 701 may be varied.

In another embodiment, for example, the operating power and timing may be provided to signal generator 704 by inducing a current from stimulator circuit 703. In this way, signal generator 704 would receive a signal indicative of the firing and value of the current provided to magnetic stimulation device 702. This current value may be translated by signal generator 704 to create the proper strength and timing for the magnetic field(s) created by surface coil 701. The current may be induced from stimulator circuit 703 using an inductive device (not shown) capable of inducing (and thus measuring) the current provided to magnetic stimulation device 702 via stimulator circuit 703.

In another embodiment, for example, surface coil 701 may operate independently of any external signal generator and power source, and simply generate its magnetic field based on the magnetic field created by magnetic stimulation device 702. Using this technique focuses on the electrical and physical characteristics of surface coil 701. In particular, surface coil 701 may be designed to react to the magnetic field created by magnetic stimulation device 702 in a way that permits therapeutic magnetic fields to penetrate the patient, while eliminating or reducing magnetic fields undesirably stimulating surface-proximate nerves, tissue and muscles.

As discussed with reference to FIGS. 1-4, surface coil 701 may be a part of a flexible circuit pad having an adhesive material that permits the pad to be affixed to a treatment location. Alternatively, surface coil 701 may be affixed to magnetic stimulation device 702. Also, where more than one surface coil 701 is used, some surface coils may be attached to a flexible circuit pad, while other surface coils may be affixed to magnetic stimulation device 702.

Figure 8:
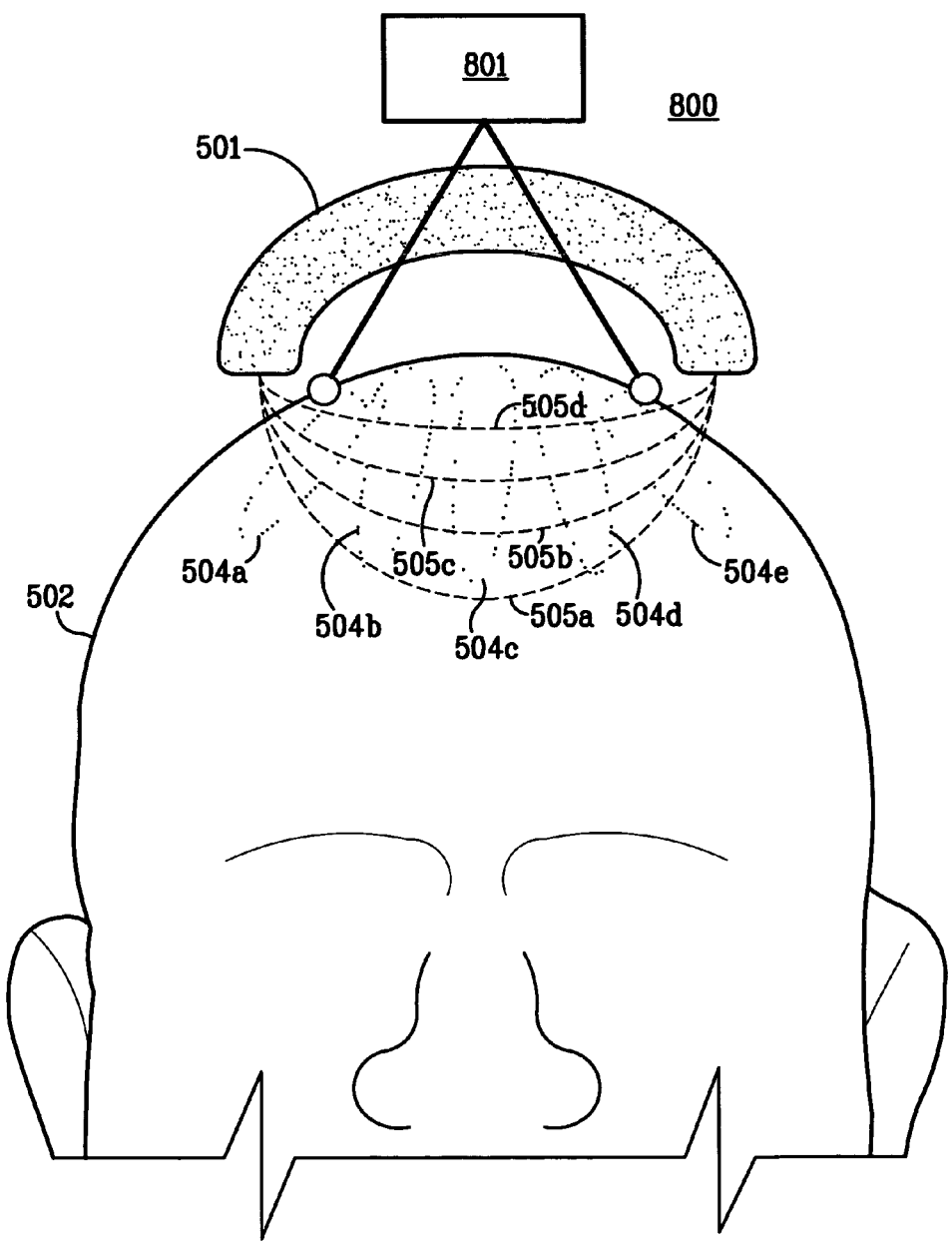
FIG. 8 is a block diagram illustrating another technique for reducing discomfort caused by transcutaneous stimulation.

FIG. 8 is a block diagram illustrating another technique for reducing discomfort caused by electrical stimulation. As shown in FIG. 8, a system 800 includes a power supply 801 in communication with electrodes 802a and 802b. Although two electrodes are shown in FIG. 8, it should be appreciated that any number of electrodes may be used.

As previously discussed, magnetic stimulation device 501 creates magnetic lines of flux 505a-d, which in turn create electric fields 504a-e. Electric fields 504a-e induce both desirable and undesirable electric currents on and within the patient's head 502. System 800 overcomes the discomfort created by the undesired electric currents, while permitting the desired electric currents to continue to have their therapeutic effect on the patient. In particular, power supply 801 provides power (i.e., current and/or voltage) to electrodes 802. Electrodes 802 conduct the power from power supply 801 to the patient's head 502.

The power provided to electrodes 802 may be substantially constant or time-varying. When the power is substantially constant, the power conducted to the patient's head 502 via electrodes 802 creates a substantially constant electric field in the nerves, muscle and tissues of the patient that lie in between or proximate to electrodes 802. The electric field created by electrodes 802 may have a strength that biases certain cells (i.e., those that are undesirably stimulated by magnetic stimulation device 501). The bias level may be such that the cells are biased near or above their depolarization level. By biasing the cells at or near their depolarization level, electrolytes for example, are redistributed along the cell, thus reducing the ability of the electrolytes from being transported across the cell membrane. Reducing the ability of the electrolytes from being transported across the cell membrane reduces the possible stimulation of those cells by magnetic stimulation device 501, because the cells may not be as capable of repeatedly responding to the induced electric field created by magnetic stimulation device 501. As a result, the discomfort felt by the patient during treatment is reduced. Although this example was discussed in the context of a substantially constant power source, it should be appreciated that the power need not be applied throughout the entire treatment, but may for example be turned off at any point after the beginning of a pulse corresponding to the therapeutic magnetic stimulation.

In addition to, or instead of, a substantially constant power supply provided when the magnetic stimulation is applied, power provided by power source 801 may be time-varying. The time-varying signal from power source 801 may be used to desensitize the muscle, tissue and/or nerves that undesirably are stimulated by magnetic stimulation device 501. In particular, power source 801 may be designed to pre-stimulate (i.e., prior to the therapeutic pulse applied by magnetic stimulation device 501) particular nerves, muscle and/or tissue to reduce their ability to undesirably respond to the otherwise therapeutic pulse.

For example, in the context of TMS, response time constants for cortical nerves typically range from 50 to 100 microseconds, while response time constants for peripheral nerves (e.g., scalp) range from 200 to 300 microseconds. Because peripheral nerves are slower to recover than the cortical nerves, stimulating the peripheral nerves just prior to application of the therapeutic magnetic stimulation reduces the peripheral nerves ability to respond to the therapeutic magnetic stimulation, and thus reduces the discomfort the patient feels as a result of the therapeutic magnetic stimulation.

Although system 800 was discussed in the context of electrodes having direct contact with the patient's head 502, it should be appreciated that system 800 also may apply electrical energy to the patient inductively, for example, using surface stimulation coils. Furthermore, while system 800 was described in the context of cortical nerves and its peripheral nerves, it should be appreciated that system 800 may apply to any circumstances where the nerves that are desired to be stimulated have an equivalent or faster response time than the nerves that are not desired to be stimulated. In addition, it should be appreciated that the required timing and frequency of the biasing or desensitizing signal provide to the patient may vary with many factors, including the characteristics of the patient and the characteristics of magnetic stimulation device 501.

System 800 also may be used in combination or independent of a drug that acts to desensitize the nerves, muscle and tissue that is undesirably stimulated by magnetic stimulation device 501. For example, a topical or injected drug may be used to desensitize or insulate the nerves, muscle and tissue from the magnetic stimulation. Such procedures may include an analgesic, anesthetic, muscle relaxant, or paralytic agent, for example. These drugs may be applied prior to the therapeutic treatment from magnetic stimulation device 501.

Figure 9:
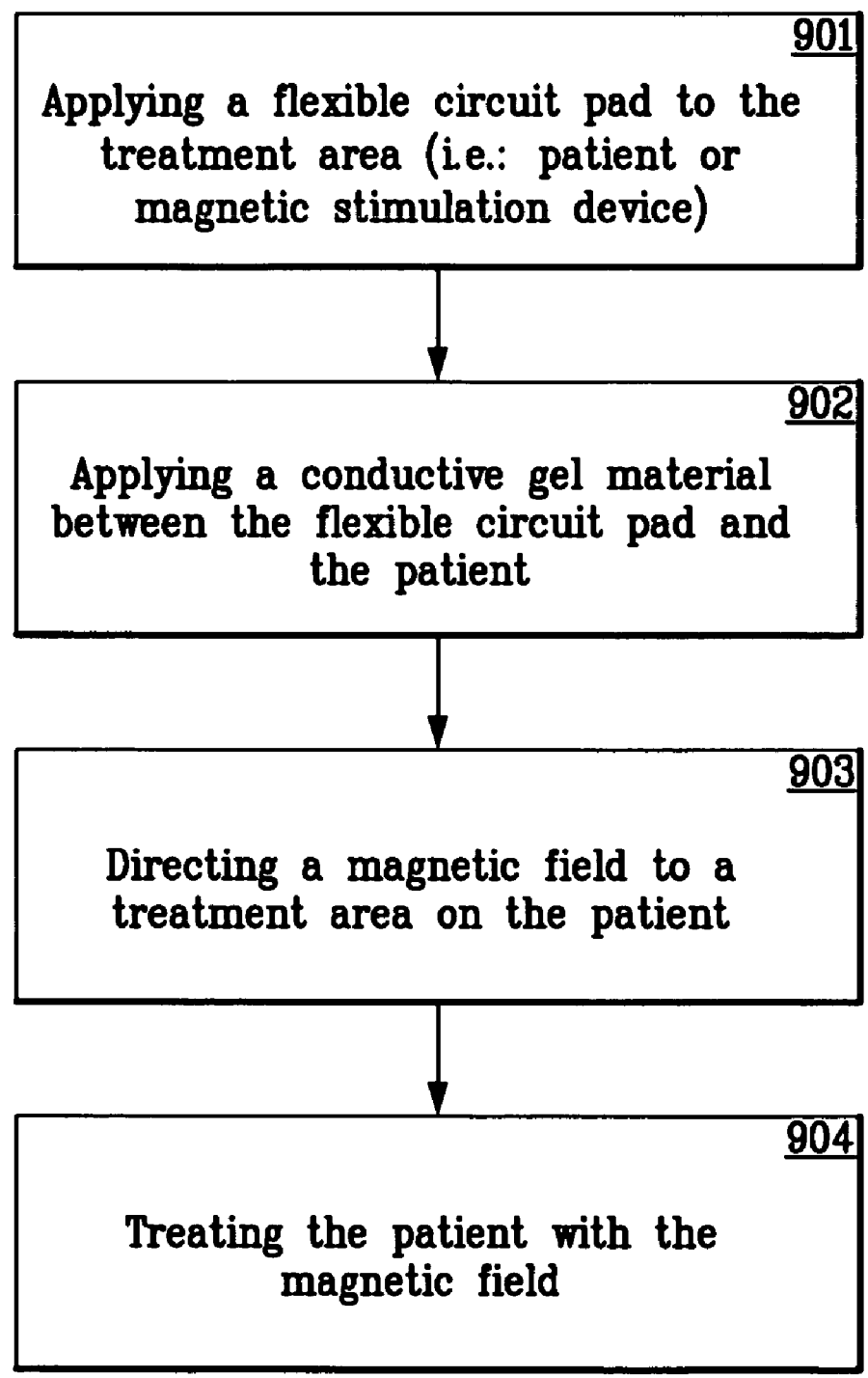
FIG. 9 is a flow diagram illustrating a technique for treating a patient using transcutaneous stimulation.

FIG. 9 is a flow diagram illustrating a technique 900 for treating a patient using transcutaneous magnetic stimulation. As shown in FIG. 9, in step 901, a magnetic field is directed to a treatment area on the patient. In step 902, a flexible circuit pad is applied to the treatment area, which may include the patient and/or magnetic stimulation device. In step 903, a conductive gel material is applied between the flexible circuit pad and the patient. In step 904, the patient is treated with the magnetic field.

Figure 10:
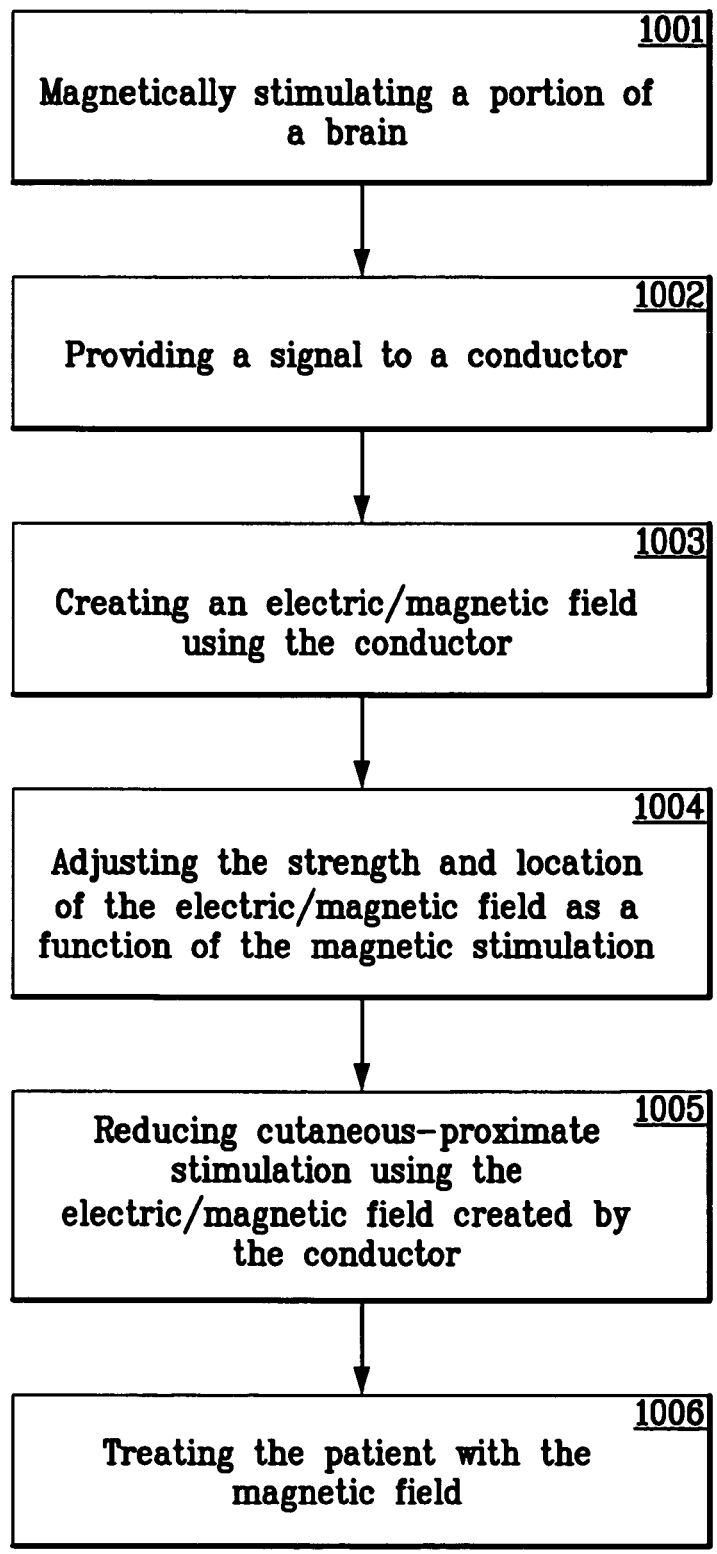
FIG. 10 is a flow diagram illustrating a technique for treating a patient using transcutaneous stimulation.
Figure 11:
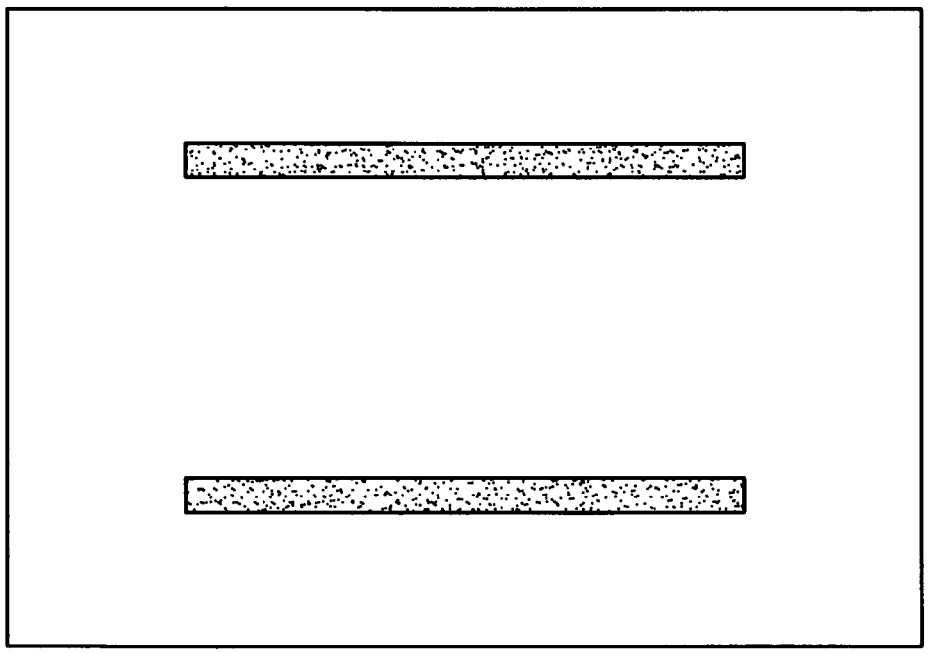
FIGS. 11-18 illustrate additional possible conductor configurations for reducing discomfort caused by transcutaneous stimulation.
Figure 12:
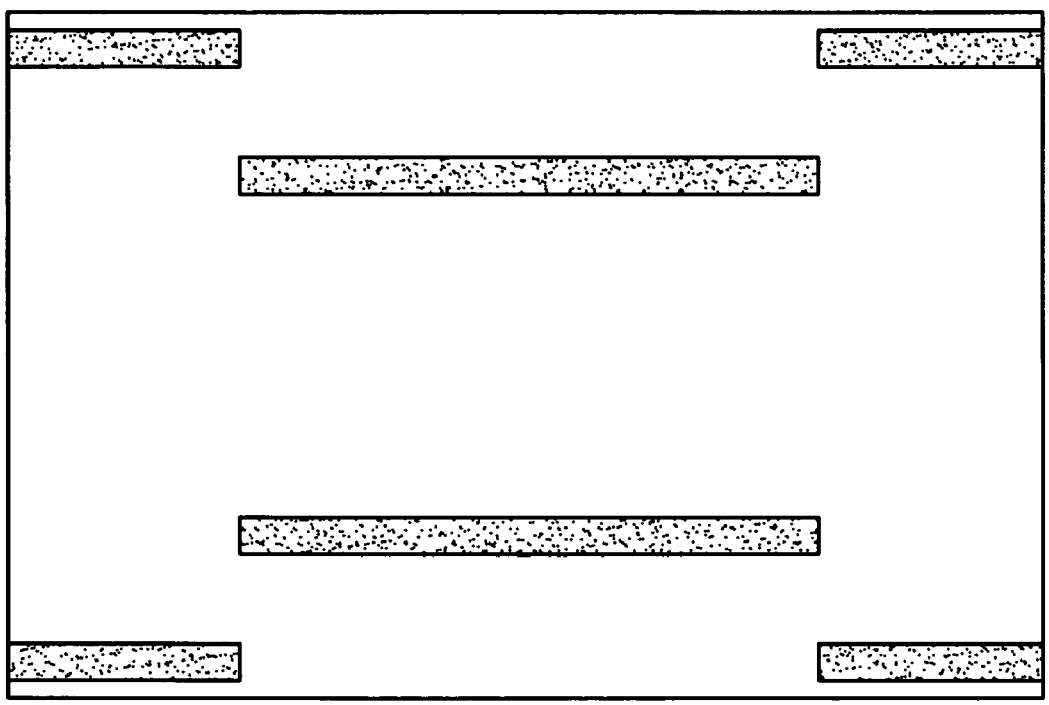
Figure 13:
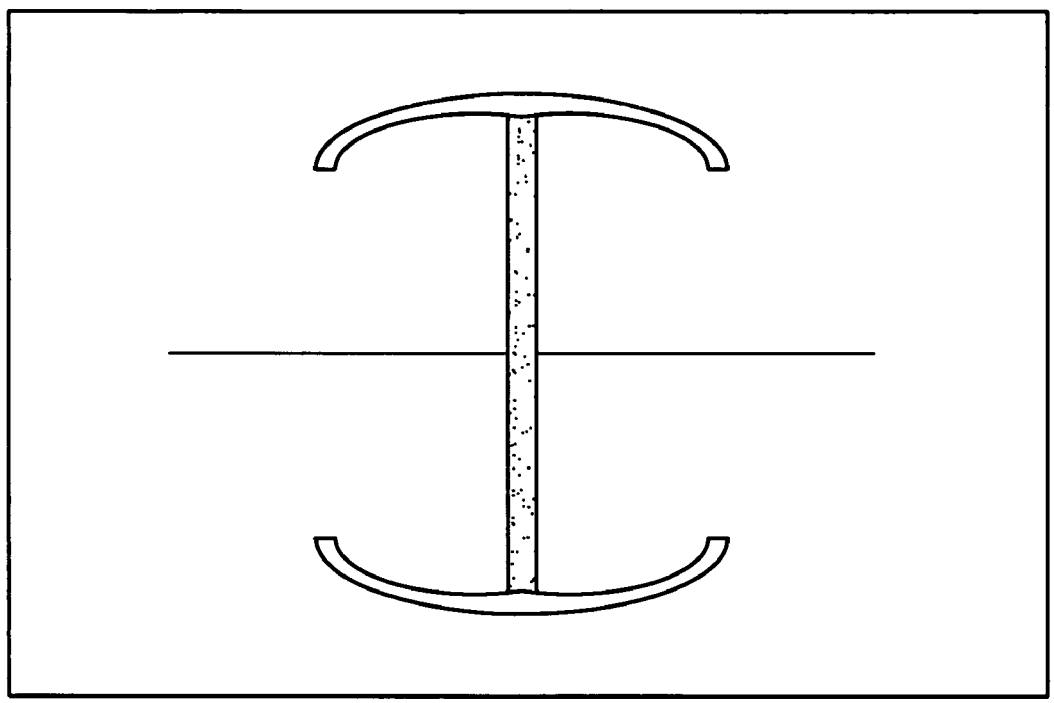
Figure 14:
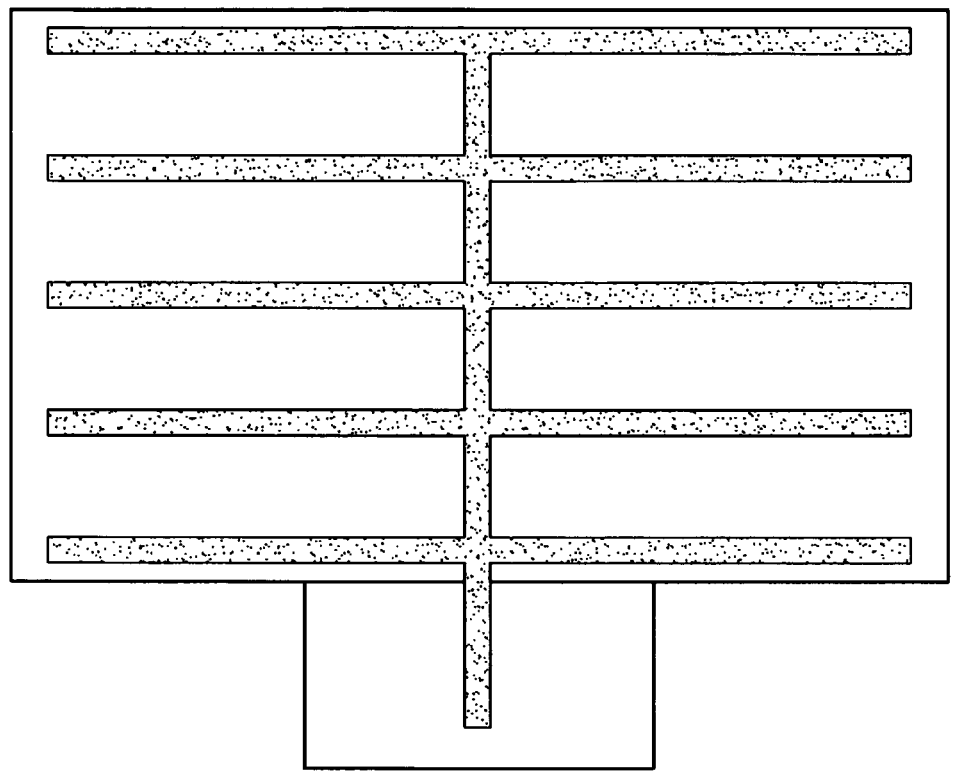
Figure 15:
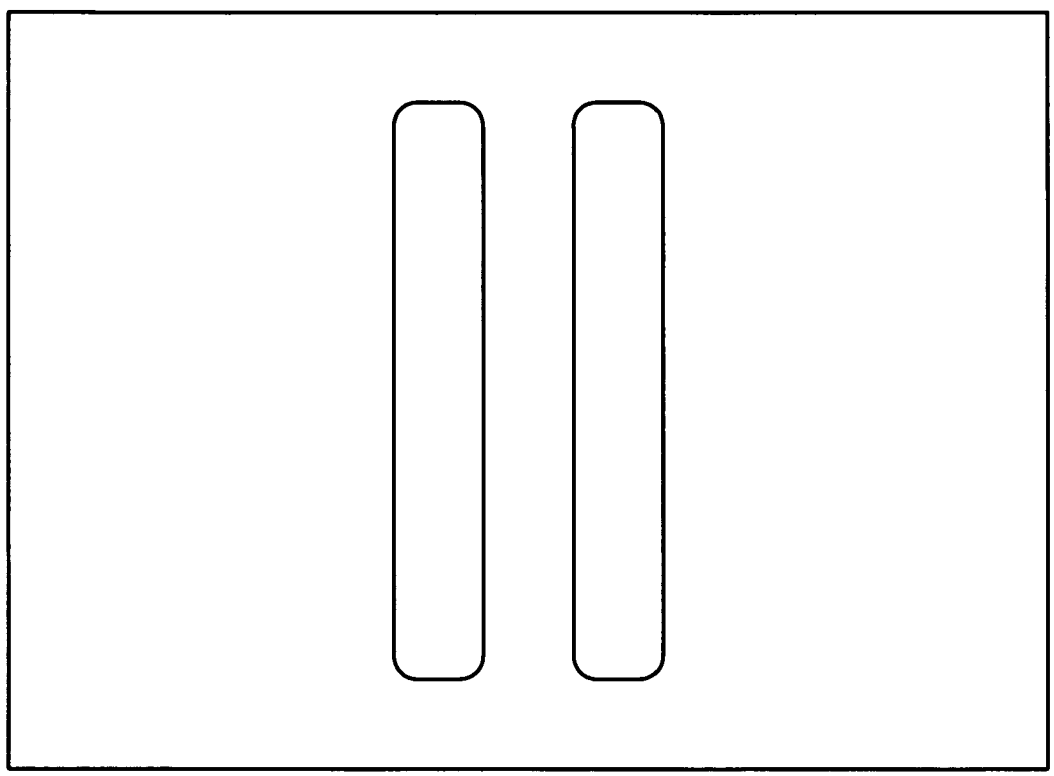
Figure 16:
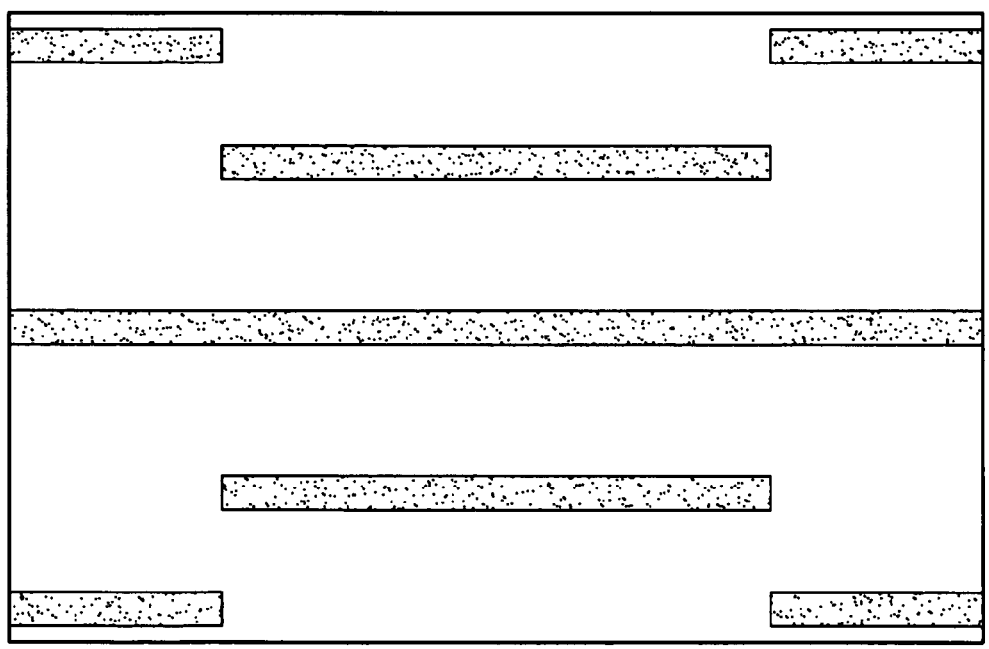
Figure 17:
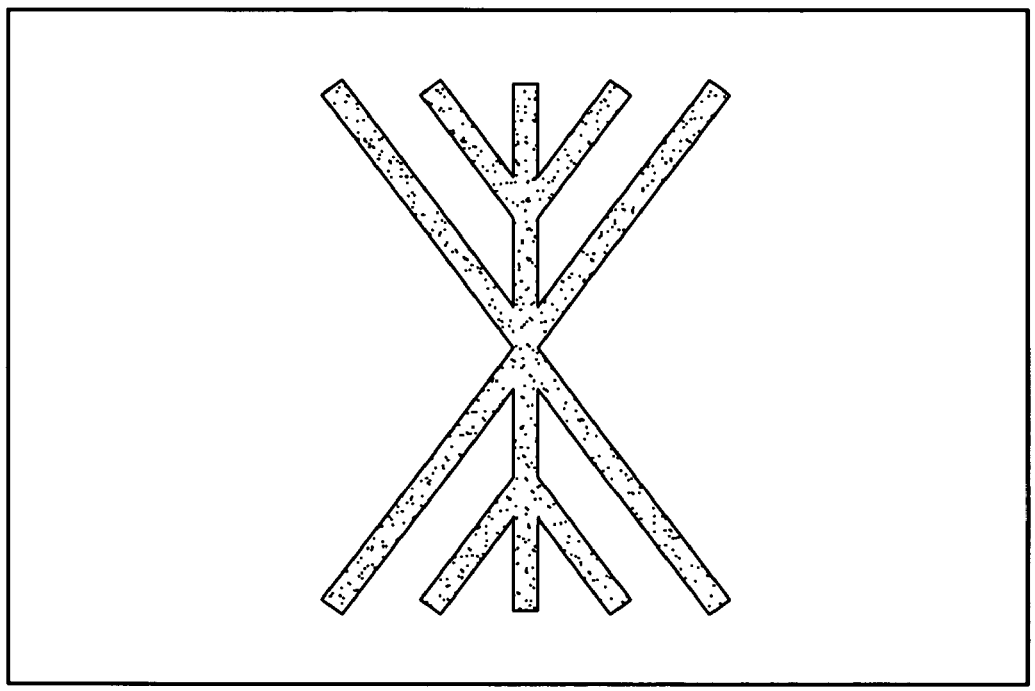
Figure 18:
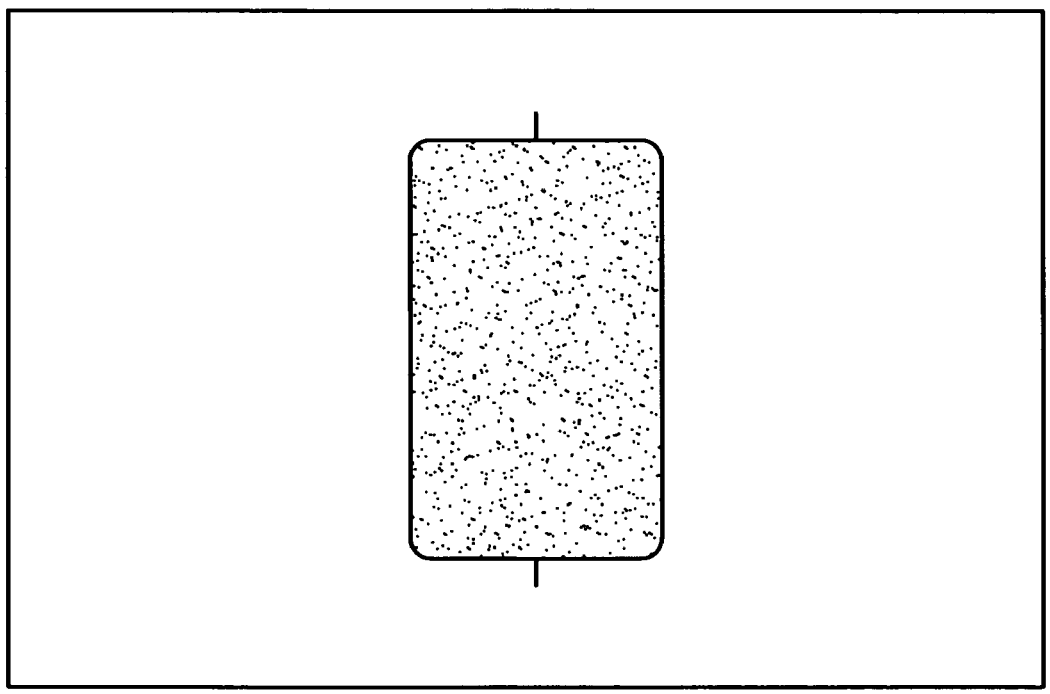

FIG. 10 is a flow diagram illustrating a technique 1000 for treating a patient using transcutaneous magnetic stimulation. As shown in FIG. 10, in step 1001, a portion of the brain is magnetically stimulated. In step 1002, a signal is provided to the conductor and in step 1003 an electric and/or magnetic field is created by the conductor. In step 1004, the strength and location of the electric and/or magnetic field is adjusted as a function of the magnetic stimulation. In step 1005, cutaneous-proximate stimulation is reduced and/or eliminated using the electric and/or magnetic fields created by the conductor. In step 1006, the patient is treated with the magnetic stimulation. The steps of technique 1000 may be accomplished using the systems described with reference to FIGS. 1-8 or any other systems.

As shown in FIGS. 11-18, additional possible conductor configurations are shown. Again, it should be appreciated that such configurations are not meant to provide exclusive, but are meant to provide further explanatory details. The invention may include any of the configurations shown, as well as any combination of those configurations.

Figure 19:
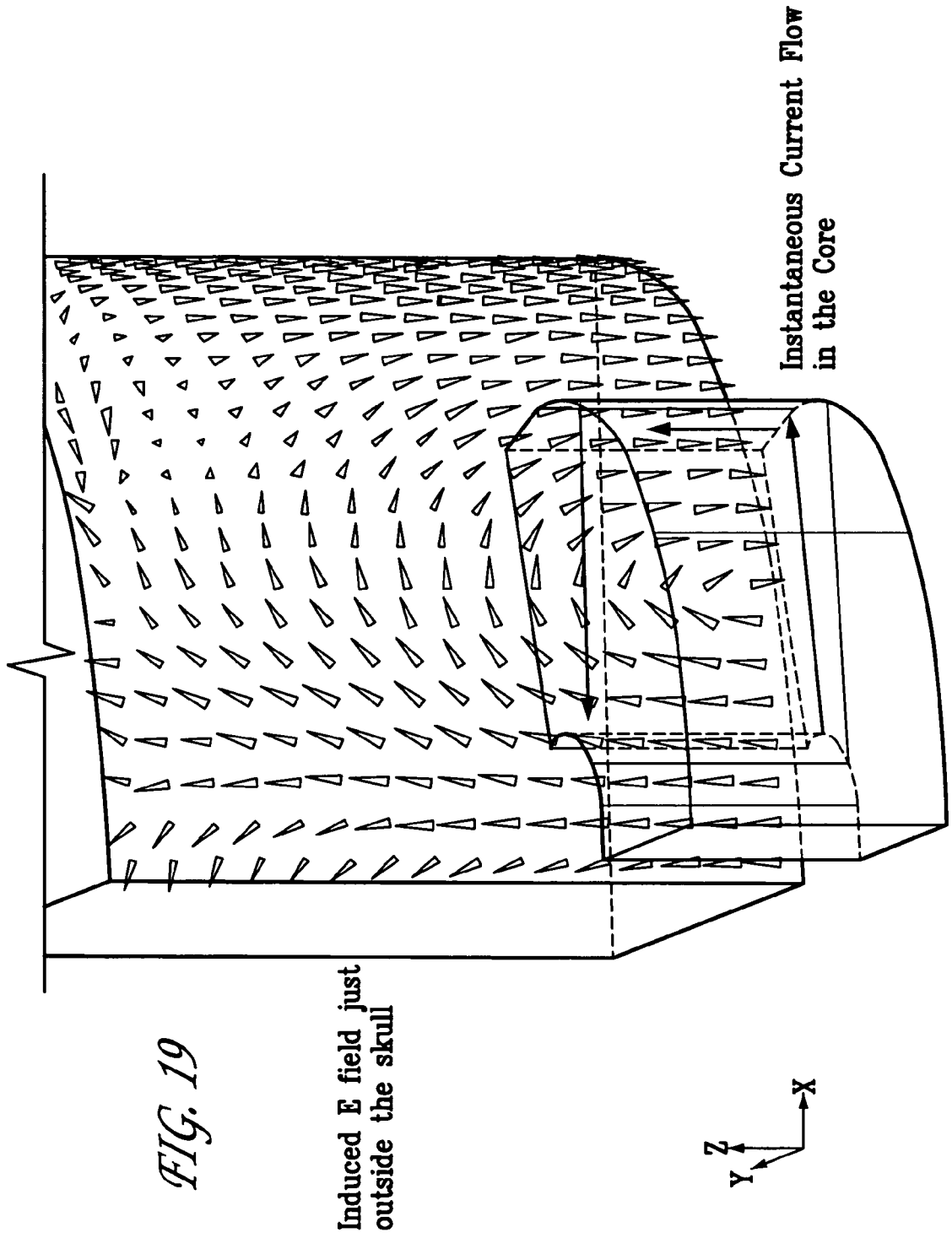
FIG. 19 provides an example of another possible conductor configuration for reducing discomfort caused by transcutaneous stimulation.

As discussed, placement and configuration of the conductors will be dependent on many variables, including the characteristics of the stimulation device, characteristics of the patient, and characteristics of the conductors, just to name in a few. Although the invention includes all such possible configurations, FIG. 19 provides one particular example for greater clarity and explanation. In one embodiment illustrated in FIG. 19, a magnetic core device may be constructed to be partially hemispherical, extend approximately 220°, and may be constructed of 3% silicone steel laminations. In this one example embodiment, the magnetic core device may be wound with eight turns of #8 American Wire Gauge (AWG) wire. The magnetic core device also may be composed of M-19 steel that saturates at 1.7 Tesla. Also, the core may be excited at 20,364 AT, RMS, which corresponds to a peak current of 3600 Amperes, delivered at 100% power. Also, the frequency of the current may be 5208 Hz, which corresponds to a period of 192 microseconds.

The magnetic field created by this device readily penetrates through the bone. In the context of TMS, where the magnetic field desirably stimulates the brain, but undesirably stimulates nerves, muscle and tissue proximate to the scalp, a three dimensional field analysis is illustrated in FIG. 19. As shown in FIG. 19, the electric field circulates around the magnetic field created by a magnetic core device 1901. Although the electric field created by magnetic core device 1901 is circular, the electric fields created by the conductors typically are not, except for the local fields produce by the conductors.

Figure 20:
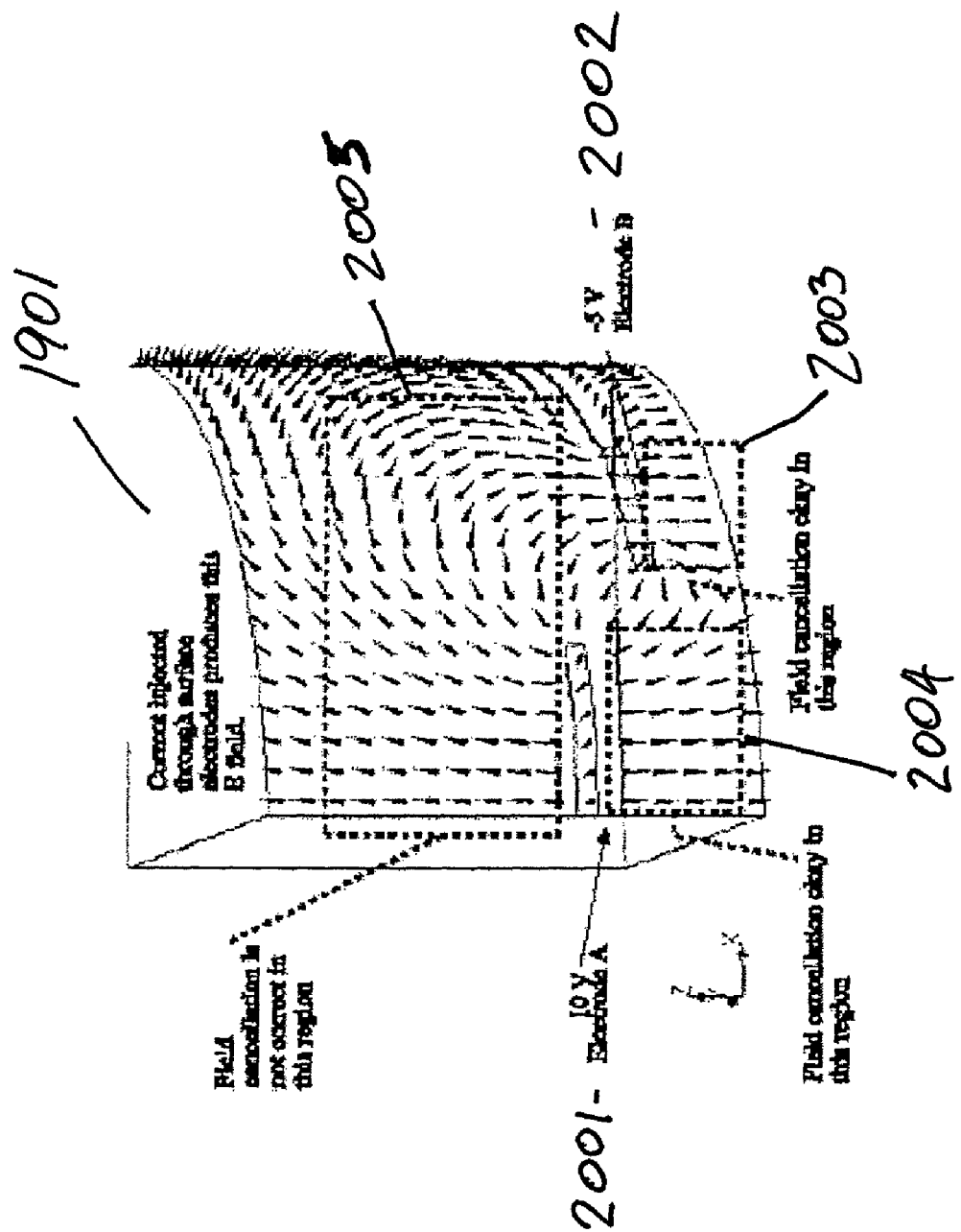

FIG. 20 illustrates one possible placement of two conductors 2001 and 2002. Conductors 2001 and 2002 are shown located with respect to the magnetic core device 1901, but it should be appreciated that the conductors may be located with reference to any object, including the patient's head, for example. In this particular example, a voltage of approximately 10 volts may be placed on conductor 2001 and a voltage of approximately −5 volts may be placed on electrode 2002.

The regions circumscribed by boxes 2003 and 2004 indicate areas where the fields created by conductors 2001 and 2002 effectively cancel or reduce the undesirable fields created by magnetic core device 1901. Also, the voltages applied to conductors 2001 and 2002 may be varied to achieve optimal cancellation or reduction of the fields in the desired regions. There also may be regions in which the fields are not optimally reduced or eliminated, such as the region circumscribed by box 2005.

In order to determine optimal conductor size, configuration and location, the electric field created by magnetic core device 1901, conductor 2001 and conductor 2002 may be considered at numerous specific points or locations and be analyzed accordingly. The electric field at any point on the surface from all three sources may be represented by the following equation:

$$\vec{E}_{total} = \{E_Z^{magA} + V_A E_Z^{elecA} - V_B E_Z^{elecB}\}\hat{a}_Z + \{E_\Phi^{magA} + V_A E_\Phi^{elecA} - V_A E_\Phi^{elecB}\}\hat{a}_\Phi \quad (1)$$

Also, the sum of all the fields may be represented by the following equation:

$$\mathcal{J} = \sum_{allpoints} \sqrt{\{E_Z^{magA} + V_A E_Z^{elec\,A} - V_B E_Z^{elecB}\}^2 + \{E_\Phi^{mag\,A} + V_A E_\Phi^{elec\,A} - V_B E_\Phi^{elecB}\}^2} \quad (2)$$

$E^{mag\,A}$ represents the value of the electric field created by magnetic core device 1901 at a particular point. Similarly, $E^{elec\,A}$ and $E^{elec\,B}$ represent the values of the electric fields created by conductor 2001 and conductor 2002, respectively, at the same or similar particular point. Also, $E_Z$ is represents the vertical electric field and $E_N$ represents the azimuthal fields. A computer simulation may be conducted to permit conductor 2001 and conductor 2002 to be varied in location, size and configuration to determine optimal field cancellation of the undesirable fields in the desired locations. For example, conductor 2001 and conductor 2002 may be allowed to move vertically, stretch out azimuthally, and have their dimensions adjusted, for example. Also, the equations may be used to determine the optimal voltages to apply to conductor 2001 ($V_A$) and to conductor 2002 ($V_B$).

FIG. 21 illustrates an embodiment where just one pair of conductors 2101 and 2102 are used to reduce the fields created by magnetic core device 1901. Typically, one conductor pair may be used to reduce or diminish fields in the area in which the device creates the strongest field concentration (e.g., for magnetic core device 1901 along the axis of the core). The voltage across conductors 2101 and 2102 may be set at 3.83 volts and the conductors each may be approximately ⅛ inch thick. The excitation signal may be 20,364 Ampere-turns at 5.2 kilohertz. Conductor 2101 and conductor 2102 each are placed approximately 0.8 inches above and below the midline of magnetic core device 1901. A one-quarter section is cut from magnetic core device 1901 to aid in visibility.

Figure 22A:
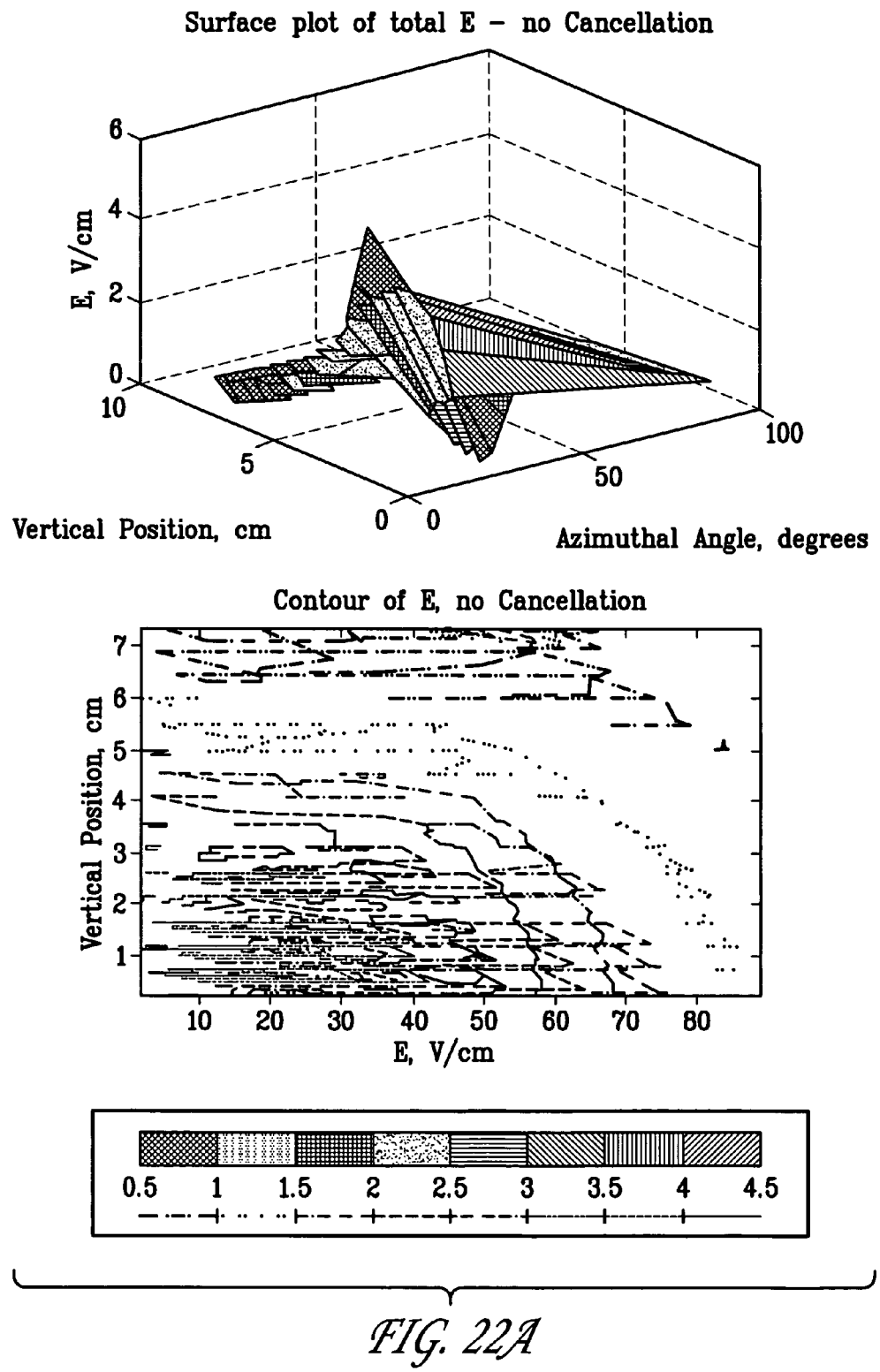
FIG. 22 graphically depicts the comparison of the electric field created by a magnetic core device both with and without cancellation by the placement of two conductors for reducing discomfort caused by transcutaneous stimulation.

FIG. 22 graphically depicts the comparison of the electric field created by magnetic core device 1901 both with and without cancellation by the conductors 2101 and 2102. In particular, as shown in FIG. 22, the presence of the conductor(s) fold the electric field pattern of magnetic core device 1901 along the core axis at Θ=0, thus shifting it away from the axis. As a result, the peak field over the surface drops from 4.91 volts/centimeter without cancellation to approximately 4.46 volts/centimeter with cancellation.

FIG. 23 illustrates an embodiment where six conductors 2301-2306 are used to reduce the fields created by magnetic core device 1901. In this particular example, the six conductors make two voltage pairs, with conductors 2301 and 2302 paired together, while conductors 2303-2306 are grouped together. As shown in FIG. 23, conductors 2303-2306 each are approximately 1.5625 inches above and below the midline of magnetic core device 1901. Also, conductors 2301 and 2302 each are 0.8125 inches above and below the midline of magnetic core device 1901. The width of conductors 2301 and 2302 each may be 2.52 inches, while the width of conductors 2303-2306 each may be 1.17 inches. A voltage of 1.86 volts may be created between conductors 2301 and 2302, while a voltage of 3.37 volts may be created between any pair of conductors 2303-2306. In addition, conductors 2301-2306 may be ⅛ inch thick.

With the conductor configuration illustrated in FIG. 23, the peak surface field of magnetic core device 1901 may be reduced from 4.91 volts/centimeter without the cancellation to 4.36 volts/centimeter with cancellation.

As discussed, the voltage waveform to the conductors should be timed with the generation of fields created by the stimulation device to maximize desirable cancellation. In particular, the voltage provided to the conductors may be timed with the current in the stimulation device. FIG. 25 provides just one example embodiment of such a possible timing configuration. As shown in FIG. 25, using a magnetic core device and stimulation circuit similar to that discussed with reference to FIGS. 19-24, for example, proper timing of the application of voltage signals to the conductors may be considered with respect to the TMS example discussed.

Figure 24:
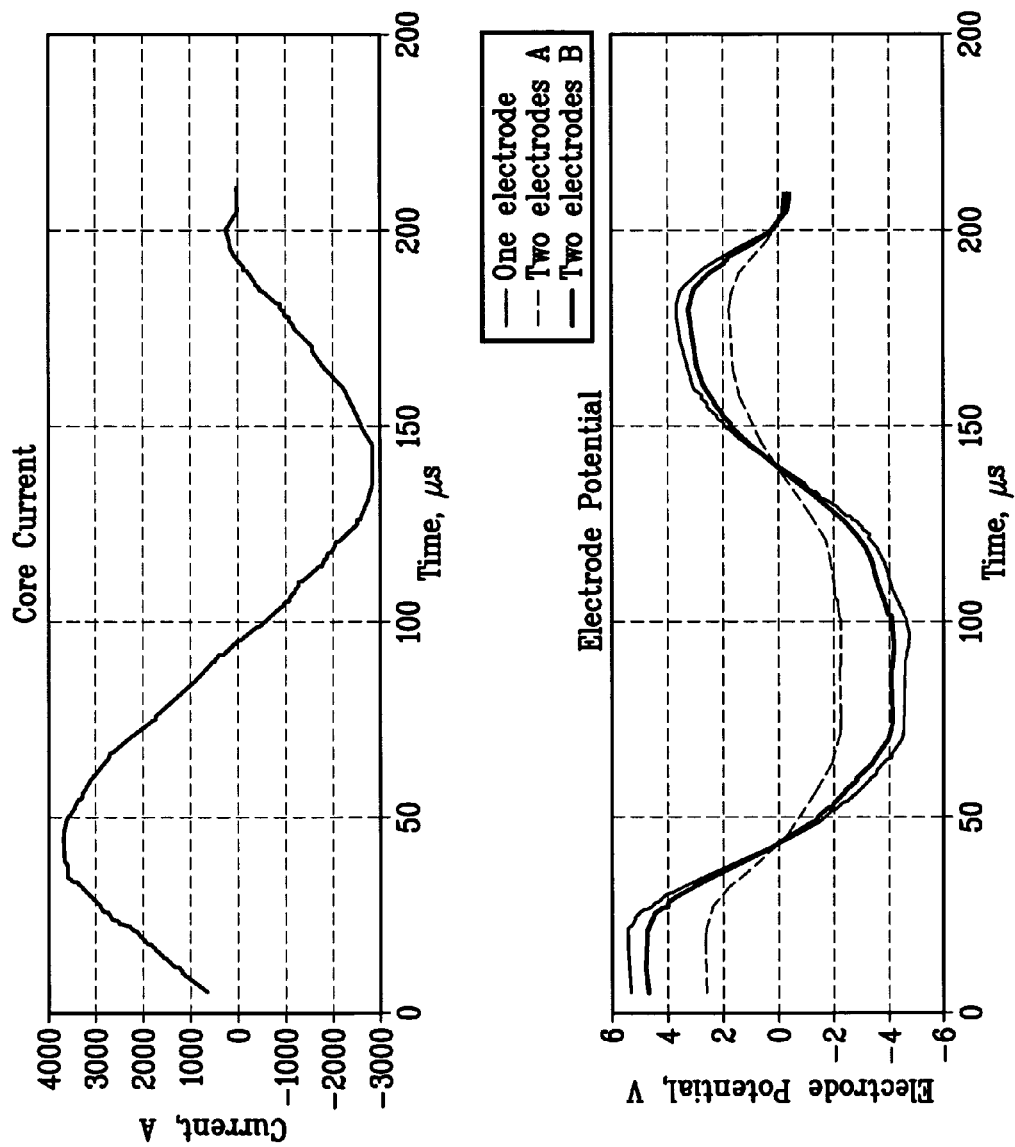

As previously discussed, voltage induced in the skin is proportional to the derivative of the magnetic field. Also, because conductivity of the stimulation device typically is relatively small, the derivative of the magnetic field created by the stimulation device is substantially similar to the derivative of the current provided to the stimulation device. In FIG. 24, the top graph illustrates that the current for magnetic core device 1901 as a function of time is a decaying sinusoid. The lower graph illustrates the accompanying conductor potential necessary to realize the field cancellation and/or reduction. Although the current begins at current may begin a zero, the voltage on the electrode does not. Table I provides an example of the values of the conductor voltage in different configurations along with the core current. Notably, as the magnetic core excitation current scales, so must the conductor voltage also scale.

TABLE I

Current and Electrode Voltage versus Time

| Time(μs) | Current (A) | One Pair (V) | Two Pair A (V) | Two Pair B (V) |
|---|---|---|---|---|
| 5 | 620 | 5.289 | 2.568 | 4.654 |
| 10 | 1100 | 5.334 | 2.590 | 4.693 |
| 15 | 1620 | 5.416 | 2.630 | 4.766 |
| 20 | 2100 | 5.406 | 2.625 | 4.757 |

TABLE I-continued

Current and Electrode Voltage versus Time

| Time(μs) | Current (A) | One Pair (V) | Two Pair A (V) | Two Pair B (V) |
|---|---|---|---|---|
| 25 | 2740 | 4.961 | 2.409 | 4.365 |
| 30 | 3100 | 3.982 | 1.934 | 3.504 |
| 35 | 3580 | 2.516 | 1.222 | 2.214 |
| 40 | 3620 | 0.858 | 0.417 | 0.755 |
| 45 | 3660 | −0.590 | −0.286 | −0.519 |
| 50 | 3500 | −1.749 | −0.849 | −1.539 |
| 55 | 3260 | −2.589 | −1.258 | −2.278 |
| 60 | 3020 | −3.307 | −1.606 | −2.909 |
| 65 | 2700 | −4.011 | −1.948 | −3.529 |
| 70 | 2220 | −4.508 | −2.189 | −3.967 |
| 75 | 1740 | −4.666 | −2.266 | −4.105 |
| 80 | 1300 | −4.640 | −2.254 | −4.083 |
| 85 | 860 | −4.619 | −2.243 | −4.064 |
| 90 | 420 | −4.677 | −2.271 | −4.115 |
| 95 | 0 | −4.788 | −2.325 | −4.213 |
| 100 | −560 | −4.715 | −2.290 | −4.148 |
| 105 | −1040 | −4.373 | −2.124 | −3.848 |
| 110 | −1320 | −4.097 | −1.990 | −3.605 |
| 115 | −1800 | −3.869 | −1.879 | −3.404 |
| 120 | −2080 | −3.515 | −1.707 | −3.093 |
| 125 | −2520 | −2.873 | −1.395 | −2.528 |
| 130 | −2720 | −1.908 | −0.927 | −1.679 |
| 135 | −2840 | −0.883 | −0.429 | −0.777 |
| 145 | −2840 | 1.082 | 0.526 | 0.952 |
| 150 | −2640 | 1.879 | 0.912 | 1.653 |
| 155 | −2440 | 2.470 | 1.200 | 2.174 |
| 160 | −2240 | 2.991 | 1.452 | 2.632 |
| 165 | −1800 | 3.290 | 1.598 | 2.894 |
| 170 | −1560 | 3.418 | 1.660 | 3.008 |
| 175 | −1200 | 3.561 | 1.729 | 3.133 |
| 180 | −920 | 3.655 | 1.775 | 3.216 |
| 185 | −480 | 3.439 | 1.670 | 3.026 |
| 190 | −160 | 2.690 | 1.306 | 2.367 |
| 195 | 100 | 1.532 | 0.744 | 1.348 |
| 200 | 220 | 0.310 | 0.150 | 0.273 |
| 205 | 0 | −0.358 | −0.174 | −0.315 |
| 210 | 0 | −0.463 | −0.225 | −0.408 |

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

What is claimed is:

1. A device for reducing discomfort caused by a magnetic stimulation device for treating a patient, comprising:
   a magnetic material adapted to be located between the magnetic stimulation device and the patient's head, wherein the magnetic material reroutes a portion of a magnetic field created by the magnetic stimulation device toward the magnetic material and reduces stimulation caused by the magnetic stimulation device at a portion of the patient's head.

2. The device of claim 1, wherein the magnetic stimulation device is adapted to be located proximate the patient's head, and wherein the magnetic stimulation device treats the patient's brain.

3. The device of claim 1, wherein the magnetic material comprises more than one structural component.

4. The device of claim 1, wherein the magnetic material is adapted to be affixed to the patient's head.

5. The device of claim 1, wherein the magnetic material is affixed to the magnetic stimulation device.

6. The device of claim 1, wherein the magnetic material is located within the magnetic stimulation device.

7. The device of claim 1, wherein the magnetic material is included within the magnetic stimulation device during manufacturing of the magnetic stimulation device.

8. The device of claim 1, wherein the magnetic material is a wire.

9. The device of claim 1, wherein the magnetic material has an arc-shaped structure spanning the length of the magnetic stimulation device.

10. The device of claim 1, wherein the magnetic material conforms to the shape of the portion of the patient to be treated.

11. The device of claim 1, wherein the magnetic material has a rectangular shape.

12. The device of claim 1, wherein the magnetic material is a sheet of material.

13. The device of claim 1, wherein the magnetic material reroutes magnetic flux lines created by magnetic stimulation device, and wherein the rerouted magnetic flux lines prevent stimulation of surface-proximate tissue.

14. The device of claim 13, wherein the magnetic material permits other magnetic flux lines to penetrate deeper within the patient for treatment purposes.

15. The device of claim 1, wherein a location of the magnetic material is adjustable as a function of at least one of the following: required reduced stimulation, a portion of the patient's anatomy to be treated, a desired strength of the magnetic field for treatment purposes.

16. The device of claim 15, wherein the location of the magnetic material is adjusted based on a movement of the magnetic material, wherein the movement is closer to the patient, closer to the magnetic stimulation device, or lateral movement along a treatment area.

17. The device of claim 1, wherein the magnetic material comprises at least one of the following: a ferrite material, a powdered iron material having a distributed gap core structure to further reduce heating concerns created by eddy currents, a combination of ferrite material and non-ferrite materials.

18. The device of claim 1, wherein other components are used to attenuate the magnetic field created by the magnetic material and directed to the magnetic stimulation device.

19. The device of claim 1, wherein the attenuation is substantially unilateral to permit magnetic fields traveling from the magnetic stimulation device to the magnetic material and attenuate magnetic fields traveling from the magnetic material to magnetic stimulation device.

20. The device of claim 1, wherein the magnetic flux lines below the magnetic material are redirected away from the patient and toward the magnetic material.

21. The device of claim 1, wherein magnetic material increases the magnetic field near the patient and leaves uninhibited the magnetic field within the patient's anatomy to be treated.

22. The device of claim 1, wherein a treatment area is a portion of a brain and wherein an area to reduce stimulation is a cutaneous-proximate area relative to the treatment area.

23. The device of claim 1, wherein the magnetic material comprises three steel wire cables having a 0.1 inch diameter and a 3 inch length.

24. The device of claim 1, wherein a longer dimension of the magnetic material is placed along a similar direction as an electric field vector induced by the magnetic stimulation device.

25. The device of claim 1, further comprising at least one conductor located peripheral to the magnetic stimulation device, wherein the conductor is adapted to reduce surface-proximate stimulation induced by the magnetic stimulation device.

26. The device of claim 25, wherein the conductor has certain physical and electrical characteristics to reduce surface-proximate stimulation induced by the magnetic stimulation device.

27. The device of claim 26, wherein the physical and electrical characteristics include at least one of the following: conductivity, inductance, length, width, aspect ratio and surface area.

28. The device of claim 25, wherein the conductor is adapted to ignore therapeutic stimulation induced by the magnetic stimulation device.

29. The device of claim 25, wherein the conductor is adapted to be located between a magnetic stimulation device and a patient.

30. The device of claim 25, wherein the conductor is attached to a flexible circuit pad.

31. The device of claim 25, wherein the conductor is a flat metallic device.

32. The device of claim 25, wherein the conductor is provided electrical energy substantially simultaneously with electrical energy provided to the magnetic stimulation device.

33. The device of claim 32, wherein the electrical energy provided to the conductor and the electrical energy provided to the magnetic stimulation device are of opposite polarity.

34. The device of claim 32, wherein the electrical energy provided to the conductor is a current that is derived from a voltage provided to the magnetic stimulation device.

35. The device of claim 1, wherein the magnetic material absorbs a portion of the magnetic field created by the magnetic stimulation device.

* * * * *